(12) United States Patent
Kostrzewski et al.

(10) Patent No.: US 9,364,217 B2
(45) Date of Patent: Jun. 14, 2016

(54) IN-SITU LOADED STAPLER

(71) Applicant: Covidien LP, Mansfield, MA (US)

(72) Inventors: Stanislaw Kostrzewski, Newtown, CT (US); Ernest Aranyi, Easton, CT (US); Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 810 days.

(21) Appl. No.: 13/652,569

(22) Filed: Oct. 16, 2012

(65) Prior Publication Data
US 2014/0103092 A1 Apr. 17, 2014

(51) Int. Cl.
| A61B 1/00 | (2006.01) |
| A61B 17/068 | (2006.01) |
| A61B 17/072 | (2006.01) |
| A61B 17/00 | (2006.01) |
| A61B 17/29 | (2006.01) |

(52) U.S. Cl.
CPC ......... *A61B 17/068* (2013.01); *A61B 17/07207* (2013.01); *A61B 2017/00398* (2013.01); *A61B 2017/00473* (2013.01); *A61B 2017/07235* (2013.01); *A61B 2017/07242* (2013.01); *A61B 2017/07271* (2013.01); *A61B 2017/07278* (2013.01); *A61B 2017/2931* (2013.01)

(58) Field of Classification Search
CPC .......... A61B 2017/07235; A61B 2017/07271; A61B 2017/07278; A61B 2017/07242
USPC ...................................... 227/178.1
See application file for complete search history.

(56) References Cited

U.S. PATENT DOCUMENTS

| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |

(Continued)

FOREIGN PATENT DOCUMENTS

| AU | 198654765 | 9/1986 |
| DE | 2744824 | 4/1978 |

(Continued)

OTHER PUBLICATIONS

Partial European Search report corresponding to European Application No. EP13188776.2, dated May 26, 2014.

(Continued)

*Primary Examiner* — Andrew M Tecco
*Assistant Examiner* — Chelsea Stinson

(57) ABSTRACT

In one aspect of the present disclosure a surgical stapling apparatus is disclosed including a cartridge assembly. The cartridge assembly includes at least one cartridge having a first half and a second half, a first row of retention slots disposed in the first half, a second row of retention slots disposed in the second half, a third row of retention slots being alternately disposed in the first half and the second half of the at least one cartridge between the first and second rows of staple receiving slots, a plurality of fasteners disposed in the retention slots of the first, second and third rows, and a plurality of pushers disposed in each of the first and second halves of the cartridge.

20 Claims, 14 Drawing Sheets

(56) References Cited

U.S. PATENT DOCUMENTS

| | | | |
|---|---|---|---|
| 4,505,414 A | 3/1985 | Filipi | |
| 4,520,817 A | 6/1985 | Green | |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,612,933 A * | 9/1986 | Brinkerhoff et al. ...... | 227/175.2 |
| 4,633,861 A | 1/1987 | Chow et al. | |
| 4,633,874 A | 1/1987 | Chow et al. | |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,869,415 A | 9/1989 | Fox | |
| 4,892,244 A | 1/1990 | Fox et al. | |
| 4,955,959 A | 9/1990 | Tompkins et al. | |
| 4,978,049 A | 12/1990 | Green | |
| 4,991,764 A | 2/1991 | Mericle | |
| 5,014,899 A | 5/1991 | Presty et al. | |
| 5,031,814 A | 7/1991 | Tompkins et al. | |
| 5,040,715 A | 8/1991 | Green et al. | |
| 5,065,929 A | 11/1991 | Schulze et al. | |
| 5,071,430 A | 12/1991 | deSalis et al. | |
| 5,074,454 A | 12/1991 | Peters | |
| 5,083,695 A | 1/1992 | Foslien et al. | |
| 5,084,057 A | 1/1992 | Green et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,156,315 A | 10/1992 | Green et al. | |
| 5,156,614 A | 10/1992 | Green et al. | |
| 5,163,943 A | 11/1992 | Mohiuddin et al. | |
| 5,170,925 A | 12/1992 | Madden et al. | |
| 5,171,247 A | 12/1992 | Hughetti et al. | |
| 5,173,133 A | 12/1992 | Morin et al. | |
| 5,180,092 A | 1/1993 | Crainich | |
| 5,188,274 A | 2/1993 | Moeinzadeh et al. | |
| 5,220,928 A | 6/1993 | Oddsen et al. | |
| 5,221,036 A | 6/1993 | Takase | |
| 5,242,457 A | 9/1993 | Akopov et al. | |
| 5,246,156 A | 9/1993 | Rothfuss et al. | |
| 5,253,793 A | 10/1993 | Green et al. | |
| 5,263,629 A | 11/1993 | Trumbull et al. | |
| RE34,519 E | 1/1994 | Fox et al. | |
| 5,275,323 A | 1/1994 | Schulze et al. | |
| 5,282,807 A | 2/1994 | Knoepfler | |
| 5,289,963 A | 3/1994 | McGarry et al. | |
| 5,307,976 A | 5/1994 | Olson et al. | |
| 5,308,576 A | 5/1994 | Green et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,330,486 A | 7/1994 | Wilk | |
| 5,332,142 A | 7/1994 | Robinson et al. | |
| 5,336,232 A | 8/1994 | Green et al. | |
| 5,344,061 A | 9/1994 | Crainich | |
| 5,352,238 A | 10/1994 | Green et al. | |
| 5,356,064 A | 10/1994 | Green et al. | |
| 5,358,506 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,366,133 A | 11/1994 | Geiste | |
| 5,376,095 A | 12/1994 | Ortiz | |
| 5,379,933 A | 1/1995 | Green et al. | |
| 5,381,943 A | 1/1995 | Allen et al. | |
| 5,382,255 A | 1/1995 | Castro et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,403,312 A | 4/1995 | Yates et al. | |
| 5,405,072 A | 4/1995 | Zlock et al. | |
| 5,407,293 A | 4/1995 | Crainich | |
| 5,413,268 A | 5/1995 | Green et al. | |
| 5,413,272 A * | 5/1995 | Green et al. ................ | 227/175.1 |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,441,193 A | 8/1995 | Gravener | |
| 5,445,304 A | 8/1995 | Plyley et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,856 A | 2/1996 | Person et al. | |
| 5,497,933 A | 3/1996 | DeFonzo et al. | |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,549,628 A | 8/1996 | Cooper et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A | 10/1996 | Huitema et al. | |
| 5,564,615 A | 10/1996 | Bishop et al. | |
| 5,571,116 A | 11/1996 | Bolanos et al. | |
| 5,573,169 A | 11/1996 | Green et al. | |
| 5,573,543 A | 11/1996 | Akopov et al. | |
| 5,575,799 A | 11/1996 | Bolanos et al. | |
| 5,575,803 A | 11/1996 | Cooper et al. | |
| 5,577,654 A | 11/1996 | Bishop | |
| 5,579,107 A | 11/1996 | Wright et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |

(56) References Cited

U.S. PATENT DOCUMENTS

| | | | |
|---|---|---|---|
| 5,597,107 | A | 1/1997 | Knodel et al. |
| 5,601,224 | A | 2/1997 | Bishop et al. |
| 5,607,095 | A | 3/1997 | Smith et al. |
| 5,615,820 | A | 4/1997 | Viola |
| 5,618,291 | A | 4/1997 | Thompson et al. |
| 5,624,452 | A | 4/1997 | Yates |
| 5,626,587 | A | 5/1997 | Bishop et al. |
| 5,628,446 | A | 5/1997 | Geiste et al. |
| 5,630,539 | A | 5/1997 | Plyley et al. |
| 5,630,540 | A | 5/1997 | Blewett |
| 5,630,541 | A | 5/1997 | Williamson, IV et al. |
| 5,632,432 | A | 5/1997 | Schulze et al. |
| 5,634,584 | A | 6/1997 | Okorocha et al. |
| 5,636,780 | A | 6/1997 | Green et al. |
| 5,645,209 | A | 7/1997 | Green et al. |
| 5,647,526 | A | 7/1997 | Green et al. |
| 5,651,491 | A | 7/1997 | Heaton et al. |
| 5,653,373 | A | 8/1997 | Green et al. |
| 5,653,374 | A | 8/1997 | Young et al. |
| 5,653,721 | A | 8/1997 | Knodel et al. |
| 5,655,698 | A | 8/1997 | Yoon |
| 5,657,921 | A | 8/1997 | Young et al. |
| 5,658,300 | A | 8/1997 | Bito et al. |
| 5,662,258 | A | 9/1997 | Knodel et al. |
| 5,662,259 | A | 9/1997 | Yoon |
| 5,662,260 | A | 9/1997 | Yoon |
| 5,662,662 | A | 9/1997 | Bishop et al. |
| 5,662,666 | A | 9/1997 | Onuki et al. |
| 5,665,085 | A | 9/1997 | Nardella |
| 5,667,517 | A | 9/1997 | Hooven |
| 5,669,544 | A | 9/1997 | Schulze et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,676,674 | A | 10/1997 | Bolanos et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,690,269 | A | 11/1997 | Bolanos et al. |
| 5,692,668 | A | 12/1997 | Schulze et al. |
| 5,697,542 | A | 12/1997 | Knodel et al. |
| 5,702,409 | A | 12/1997 | Rayburn et al. |
| 5,704,534 | A | 1/1998 | Huitema et al. |
| 5,706,997 | A | 1/1998 | Green et al. |
| 5,709,334 | A | 1/1998 | Sorrentino et al. |
| 5,711,472 | A | 1/1998 | Bryan |
| 5,713,505 | A | 2/1998 | Huitema |
| 5,715,988 | A | 2/1998 | Palmer |
| 5,716,366 | A | 2/1998 | Yates |
| 5,718,359 | A | 2/1998 | Palmer |
| 5,725,536 | A | 3/1998 | Oberlin et al. |
| 5,725,554 | A | 3/1998 | Simon et al. |
| 5,728,110 | A | 3/1998 | Vidal et al. |
| 5,732,806 | A | 3/1998 | Foshee et al. |
| 5,735,848 | A | 4/1998 | Yates et al. |
| 5,743,456 | A | 4/1998 | Jones et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,256 | A | 6/1998 | Mastri et al. |
| 5,769,303 | A | 6/1998 | Knodel et al. |
| 5,769,892 | A | 6/1998 | Kingwell |
| 5,772,099 | A | 6/1998 | Gravener |
| 5,772,673 | A | 6/1998 | Cuny et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,834 | A | 7/1998 | Lucey et al. |
| 5,785,232 | A | 7/1998 | Vidal et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,811 | A | 9/1998 | Yates et al. |
| 5,810,855 | A | 9/1998 | Rayburn et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,109 | A | 10/1998 | McGarry et al. |
| 5,820,009 | A | 10/1998 | Melling et al. |
| 5,823,066 | A | 10/1998 | Huitema et al. |
| 5,826,776 | A | 10/1998 | Schulze et al. |
| 5,829,662 | A | 11/1998 | Allen et al. |
| 5,833,695 | A | 11/1998 | Yoon |
| 5,836,147 | A | 11/1998 | Schnipke |
| 5,862,972 | A | 1/1999 | Green et al. |
| 5,865,361 | A * | 2/1999 | Milliman et al. .......... 227/176.1 |
| 5,871,135 | A | 2/1999 | Williamson, IV et al. |
| 5,873,873 | A | 2/1999 | Smith et al. |
| 5,878,938 | A | 3/1999 | Bittner et al. |
| 5,893,506 | A | 4/1999 | Powell |
| 5,894,979 | A | 4/1999 | Powell |
| 5,897,562 | A | 4/1999 | Bolanos et al. |
| 5,901,895 | A | 5/1999 | Heaton et al. |
| 5,911,352 | A | 6/1999 | Racenet et al. |
| 5,911,353 | A | 6/1999 | Bolanos et al. |
| 5,918,791 | A | 7/1999 | Sorrentino et al. |
| 5,919,198 | A | 7/1999 | Graves, Jr. et al. |
| 5,922,001 | A | 7/1999 | Yoon |
| 5,931,847 | A | 8/1999 | Bittner et al. |
| 5,941,442 | A | 8/1999 | Geiste et al. |
| 5,954,259 | A | 9/1999 | Viola et al. |
| 5,964,774 | A | 10/1999 | McKean et al. |
| 5,980,510 | A | 11/1999 | Tsonton et al. |
| 5,988,479 | A | 11/1999 | Palmer |
| 6,004,335 | A | 12/1999 | Vaitekunas et al. |
| 6,010,054 | A | 1/2000 | Johnson et al. |
| 6,032,849 | A | 3/2000 | Mastri et al. |
| 6,045,560 | A | 4/2000 | McKean et al. |
| 6,063,097 | A | 5/2000 | Oi et al. |
| 6,079,606 | A | 6/2000 | Milliman et al. |
| 6,099,551 | A | 8/2000 | Gabbay |
| 6,109,500 | A | 8/2000 | Alli et al. |
| 6,131,789 | A | 10/2000 | Schulze et al. |
| 6,131,790 | A | 10/2000 | Piraka |
| 6,155,473 | A | 12/2000 | Tompkins et al. |
| 6,197,017 | B1 | 3/2001 | Brock et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,269,977 | B1 | 8/2001 | Moore |
| 6,279,809 | B1 | 8/2001 | Nicolo |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,391,038 | B2 | 5/2002 | Vargas et al. |
| 6,398,797 | B2 | 6/2002 | Bombard et al. |
| 6,436,097 | B1 | 8/2002 | Nardella |
| 6,439,446 | B1 | 8/2002 | Perry et al. |
| 6,443,973 | B1 | 9/2002 | Whitman |
| 6,463,623 | B2 | 10/2002 | Ahn et al. |
| 6,478,804 | B2 | 11/2002 | Vargas et al. |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,602,252 | B2 | 8/2003 | Mollenauer |
| 6,612,053 | B2 | 9/2003 | Liao |
| 6,619,529 | B2 | 9/2003 | Green et al. |
| D480,808 | S | 10/2003 | Wells et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,681,978 | B2 | 1/2004 | Geiste et al. |
| 6,698,643 | B2 | 3/2004 | Whitman |

(56) References Cited

U.S. PATENT DOCUMENTS

| | | | |
|---|---|---|---|
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielson et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 * | 7/2008 | Holsten et al. ............ 227/176.1 |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Gillum et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |

(56) References Cited

U.S. PATENT DOCUMENTS

| | | |
|---|---|---|
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton et al. |
| 7,740,160 B2 | 6/2010 | Viola |
| 7,743,960 B2 | 6/2010 | Whitman |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |

(56) References Cited

U.S. PATENT DOCUMENTS

| | | | |
|---|---|---|---|
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk et al. |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,151 B2 | 4/2012 | Ingmanson et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,558 B2 | 5/2012 | Sapienza |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,236,010 B2 | 8/2012 | Ortiz et al. |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,252,009 B2 | 8/2012 | Weller et al. |
| 8,267,300 B2 | 9/2012 | Boudreaux |
| 8,272,554 B2 | 9/2012 | Whitman et al. |
| 8,763,876 B2 * | 7/2014 | Kostrzewski ............... 227/176.1 |
| 2004/0108357 A1 | 6/2004 | Milliman |
| 2004/0199180 A1 | 10/2004 | Knodel et al. |
| 2004/0199181 A1 | 10/2004 | Knodel et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0103819 A1 | 5/2005 | Racenet |
| 2005/0119669 A1 | 6/2005 | Demmy |
| 2005/0189397 A1 | 9/2005 | Jankowski |
| 2005/0216055 A1 | 9/2005 | Scirica et al. |
| 2006/0049229 A1 | 3/2006 | Milliman et al. |
| 2006/0180634 A1 | 8/2006 | Shelton, IV et al. |
| 2006/0289602 A1 | 12/2006 | Wales et al. |
| 2007/0027469 A1 | 2/2007 | Smith et al. |
| 2007/0073341 A1 | 3/2007 | Smith et al. |
| 2007/0084897 A1 | 4/2007 | Shelton, IV et al. |
| 2007/0084899 A1 | 4/2007 | Taylor |
| 2007/0102472 A1 | 5/2007 | Shelton, IV |
| 2007/0106317 A1 | 5/2007 | Shelton, IV |
| 2007/0119901 A1 | 5/2007 | Ehrenfels et al. |
| 2007/0145096 A1 | 6/2007 | Viola et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |

(56) References Cited

U.S. PATENT DOCUMENTS

| | | |
|---|---|---|
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0110961 A1 | 5/2008 | Voegele et al. |
| 2008/0149685 A1 | 6/2008 | Smith et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296344 A1 | 12/2008 | Cropper et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0065549 A1 | 3/2009 | Viola |
| 2009/0078739 A1 | 3/2009 | Viola |
| 2009/0090763 A1 | 4/2009 | Zemlok et al. |
| 2009/0090766 A1 | 4/2009 | Knodel |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277946 A1 | 11/2009 | Marczyk |
| 2009/0277949 A1 | 11/2009 | Viola et al. |
| 2009/0283568 A1 | 11/2009 | Racenet et al. |
| 2009/0306708 A1 | 12/2009 | Shah |
| 2009/0308907 A1 | 12/2009 | Nalagatla et al. |
| 2010/0012703 A1 | 1/2010 | Calabrese et al. |
| 2010/0012704 A1 | 1/2010 | Racenet et al. |
| 2010/0069942 A1 | 3/2010 | Shelton, IV et al. |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith |
| 2010/0116867 A1 | 5/2010 | Balbierz et al. |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0245578 A1 | 10/2011 | Wazer et al. |
| 2011/0253765 A1 | 10/2011 | Nicholas et al. |
| 2011/0257679 A1 | 10/2011 | Ishitsuki et al. |

FOREIGN PATENT DOCUMENTS

| | | |
|---|---|---|
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |

(56) References Cited

FOREIGN PATENT DOCUMENTS

| | | |
|---|---|---|
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 2 130 498 A1 | 12/2009 |
| EP | 2687163 A1 | 1/2014 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 6/1975 |
| SU | 659146 | 4/1979 |
| SU | 728848 | 5/1980 |
| SU | 980703 | 12/1982 |
| SU | 990220 | 1/1983 |
| WO | WO 8302247 | 7/1983 |
| WO | WO 89/10094 | 11/1989 |
| WO | WO 9210976 | 7/1992 |
| WO | WO 9308754 | 5/1993 |
| WO | WO 9314706 | 8/1993 |
| WO | WO 2010/054404 A1 | 5/2010 |

OTHER PUBLICATIONS

Partial European Search report corresponding to European Application No. EP13188776.2, dated Feb. 3, 2014; 9 pages.

European Examination Report dated Apr. 8, 2015 from Application No. EP 13188776.2.

* cited by examiner

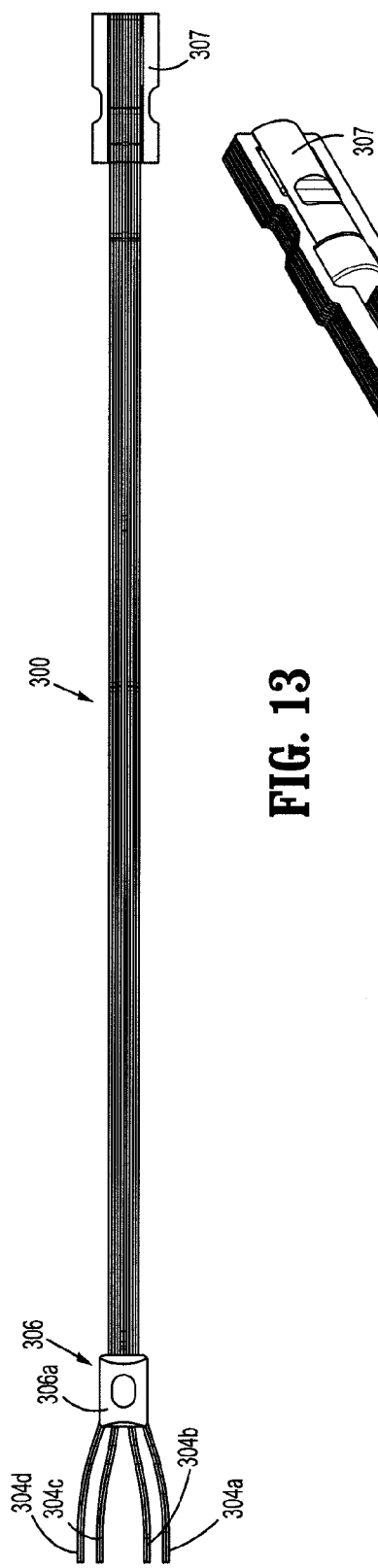
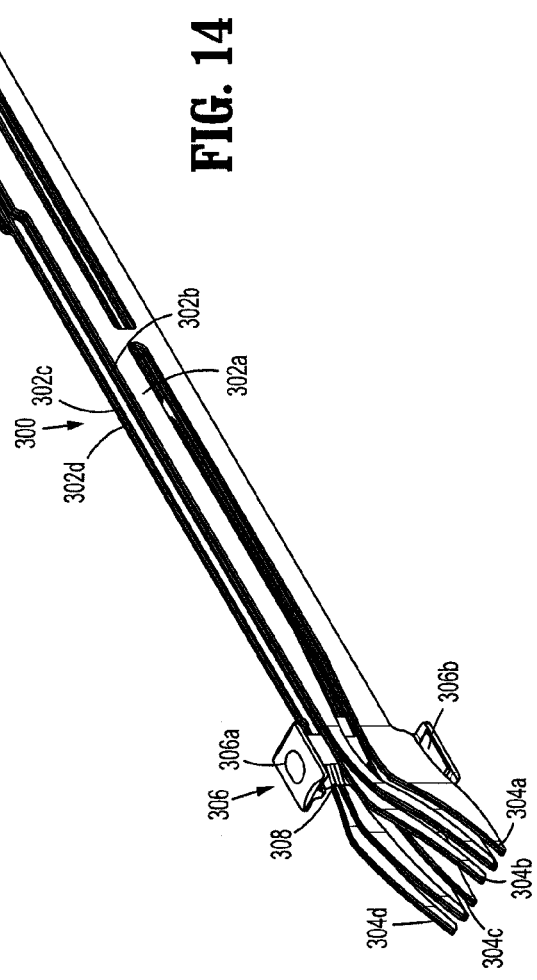
FIG. 13
FIG. 14

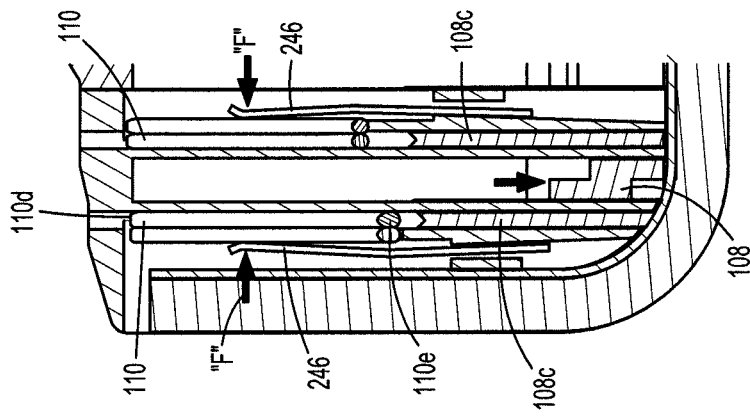
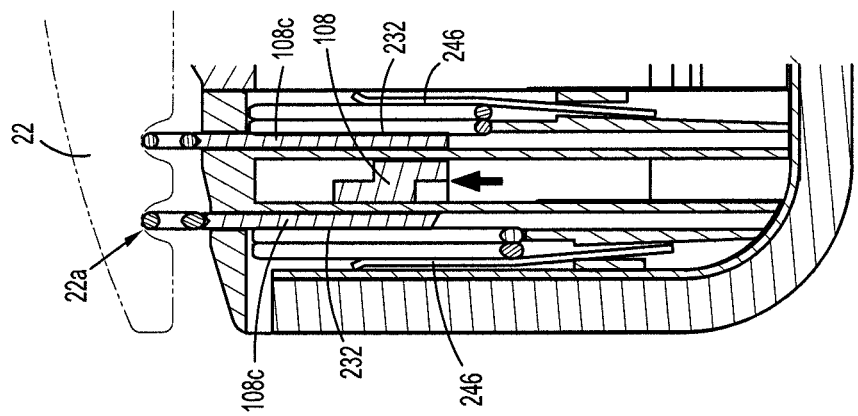
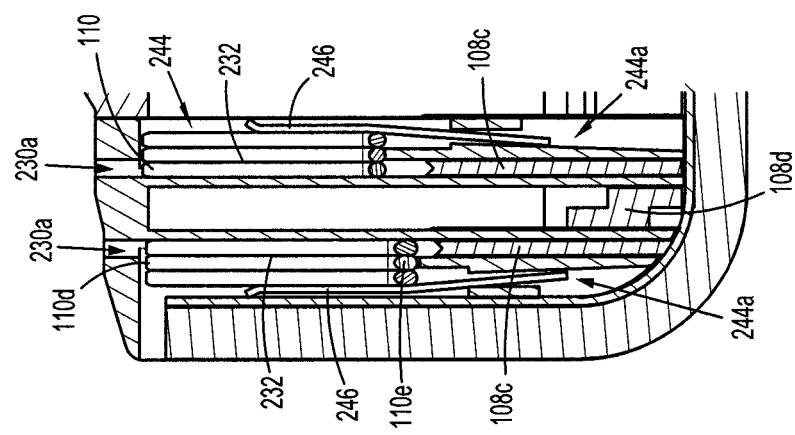

IN-SITU LOADED STAPLER

BACKGROUND

1. Technical Field

This application relates to a surgical stapling apparatus, and more particularly, to a cartridge assembly including multiple cartridge halves and a magazine for reloading the surgical stapling apparatus in-situ.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by a cam bar, a drive sled or other similar mechanism, that travels longitudinally through the staple cartridge and acts upon the staple pushers to sequentially eject the staples from the staple cartridge. A knife can travel between the staple rows to longitudinally cut and/or open the stapled tissue between the rows of staples. Some staplers apply a double row of staples on each side of the incision by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit.

In endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed. An example of an endoscopic surgical stapling device is disclosed, for example, in U.S. Pat. No. 8,070,033 to Milliman et al., the entire contents of which is incorporated herein by reference.

It would be extremely beneficial to provide a surgical device for use during laparoscopic and/or endoscopic surgical procedures that can be employed to provide multiple firings of the surgical device without requiring removal of the surgical device from the surgical site.

SUMMARY

In accordance with the present disclosure, a surgical stapling apparatus for sequentially applying a plurality of fasteners to body tissue and simultaneously incising tissue is provided. The surgical stapling apparatus is configured to receive a disposable loading unit including a plurality of retention slots disposed in a plurality of rows for receiving a plurality of staples therein. Each retention slot includes a staple magazine operatively associated therewith for supplying staples for subsequent firing.

In one aspect of the present disclosure a surgical stapling apparatus is disclosed including a handle assembly, an elongated body extending distally from the handle assembly and defining a longitudinal axis, and a disposable loading unit supported at the distal end of the elongated body. The disposable loading unit includes an anvil assembly and a cartridge assembly. The cartridge assembly includes at least one cartridge having a first half and a second half, a first row of retention slots disposed in the first half of the at least one cartridge, a second row of retention slots disposed in the second half of the at least one cartridge, a third row of retention slots being alternately disposed in the first half and the second half of the at least one cartridge between the first and second rows of staple receiving slots, a plurality of fasteners disposed in the retention slots of the first, second and third rows, and a plurality of pushers disposed in each of the first and second halves of the cartridge. Each pusher is disposed in operative association with at least one of the retention slots of the cartridge assembly and is configured to eject a respective fastener from the at least one retention slot during firing of the surgical stapling apparatus.

In an aspect of the present disclosure, the at least one cartridge is a pair of cartridges configured to couple together at a distal end portion thereof and defining a longitudinal slot therebetween when coupled together.

In an aspect of the present disclosure, the longitudinal slot is configured to facilitate passage of a knife blade therethrough.

In an aspect of the present disclosure, the first and second halves of the at least one cartridge include corresponding flanges and channels. The channels of the first and second halves are configured to receive corresponding flanges of the first and second halves, respectively, when the first and second halves are coupled together.

In an aspect of the present disclosure, the flanges of the first and second halves include the retention slots of the second row therein.

In an aspect of the present disclosure, the cartridge assembly further includes a cartridge support channel configured to receive the first and second halves of the at least one cartridge therein to maintain the first and second halves in engagement with one another.

In an aspect of the present disclosure, each retention slot of the at least one cartridge includes a staple magazine disposed in operative association therewith and including a plurality of fasteners therein. The staple magazine is configured to supply one of the plurality of fasteners of the staple magazine to the corresponding retention slot after a firing of the surgical stapling device.

In an aspect of the present disclosure, the plurality of fasteners disposed in the retention slots and staple magazines of the first row have a first size, the plurality of fasteners disposed in the retention slots and staple magazines of the second row have a second size, and the plurality of fasteners disposed in the retention slots and staple magazines of the third row have a third size. In an aspect of the present disclosure the first, second and third sizes are substantially the same. In another aspect of the present disclosure, the first size is greater than the second and third sizes and the third size is greater than the second size. In another aspect of the present disclosure, the first size is greater than the second and third sizes and the second and third sizes are the same. In another aspect of the present disclosure, the first and second sizes are the same and the third size is smaller than the first and second sizes.

In an aspect of the present disclosure, the first half defines a first tissue contacting surface, the second half defines a second tissue contacting surface, and the first and second halves, when coupled together, define a third tissue contacting surface. In an aspect of the present disclosure, it is contemplated that a height of each of the first and second tissue contacting surfaces is substantially the same, that a height of the first and third tissue contacting surfaces is substantially the same, that a height of the second and third tissue contacting surfaces is substantially the same or that a height of each of the first, second and third tissue contacting surfaces is substantially the same. In another aspect of the present disclosure, the height of the first tissue contacting surface is greater than one or both of the heights of the second and third tissue contacting surfaces. In another aspect of the present disclosure, the height of the second tissue contacting surface is greater than one or both of the heights of the first and third tissue contacting surfaces. In another aspect of the present disclosure, the height of the third tissue contacting surface is greater than one or both of the heights of the first and second tissue contacting surfaces.

In an aspect of the present disclosure, the staple magazine includes a biasing member configured to bias the plurality of fasteners disposed in the staple magazine toward the corresponding retention slot. In an aspect of the present disclosure, the biasing member is a leaf spring.

In an aspect of the present disclosure, each of the plurality of pushers includes at least one pusher plate disposed within at least one of the retention slots of the first, second and third rows. The at least one pusher plate is configured to translate through the respective retention slot to eject the respective fastener disposed therein.

In an aspect of the present disclosure, each of the plurality of pushers is configured to cover an opening disposed between a respective retention slot and the corresponding staple magazine when translating through the respective retention slot to a fired position to eject the respective fastener disposed therein, and to uncover the opening disposed between the respective retention slot and the corresponding staple magazine when translating back to a pre-fired position after the respective fastener has been ejected from the respective retention slot, thereby allowing the corresponding staple magazine to re-supply the respective retention slot with one of the plurality of fasteners disposed in the corresponding staple magazine.

In an aspect of the present disclosure, the surgical stapling apparatus includes a firing cam assembly that is translatably disposed within the disposable loading unit. The firing cam assembly includes a plurality of drive bars. Each drive bar includes a firing cam disposed at a distal end thereof and is configured to translate through one of the first and second halves of the at least one cartridge to engage and drive each pusher to eject the fastener from the corresponding retention slot during firing of the surgical stapling apparatus.

In an aspect of the present disclosure, each of the first and second halves of the at least one cartridge includes a longitudinal slot extending therethrough configured for the reception of one of the plurality of drive bars therethrough.

In an aspect of the present disclosure, each firing cam includes a camming slot configured to receive the plurality of pushers therein during a distal translation of the firing cam assembly to translate the plurality of pushers between a pre-fired position and a fired position.

In an aspect of the present disclosure, each pusher includes a proximal camming surface and each camming slot of each firing cam includes a firing cam surface. The firing cam surface is configured to engage the proximal camming surface of the pusher during distal translation of the respective drive bar to translate the pusher to the fired position and cause the pusher to eject the respective fastener from the at least one retention slot.

In an aspect of the present disclosure, each pusher includes a distal camming surface and each camming slot includes a retracting cam surface. The retracting cam surface is configured to engage the distal camming surface of the pusher during proximal translation of the respective drive bar to cause the pusher to return to the pre-fired position.

In an aspect of the present disclosure, each camming slot includes a proximal portion proximal of the firing cam surface that is configured to maintain each pusher disposed therein in the fired position.

In an aspect of the present disclosure, a surgical stapling apparatus is disclosed including a handle assembly, an elongated body extending distally from the handle assembly and defining a longitudinal axis, and a disposable loading unit supported at the distal end of the elongated body. The disposable loading unit includes an anvil assembly and a cartridge assembly. The cartridge assembly includes a plurality of retention slots disposed in a plurality of rows, each retention slot including a fastener disposed therein, and a staple magazine disposed in operative association with each retention slot. The staple magazine includes a plurality of fasteners and a biasing member disposed therein. The biasing member is configured to bias the plurality of fasteners towards the corresponding retention slot. The staple magazine is configured to reload the corresponding retention slot with one of the plurality of fasteners after a firing of the surgical stapling apparatus.

In an aspect of the present disclosure, the plurality of rows of retention slots include at least a first row of retention slots and a second row of retention slots. In an aspect of the present disclosure, the fasteners disposed in the first row of retention slots have a first size and the fasteners disposed in the second row of retention slots having a second size. In an aspect of the present disclosure, the first size is substantially equal to the second size. In another aspect of the present disclosure, the first size is greater than the second size. In another aspect of the present disclosure, the second size is greater than the first size.

In an aspect of the present disclosure, the plurality of fasteners of each staple magazine corresponding to the retention slots of the first row have the first size and the plurality of fasteners of each staple magazine corresponding to the retention slots of the second row have the second size.

In an aspect of the present disclosure, a cartridge assembly for use with a disposable loading unit of a surgical stapling apparatus is disclosed including a first cartridge and a second cartridge coupled to the first cartridge. Each of the first and second cartridges includes a first cartridge half and a second cartridge half and each cartridge half includes a longitudinal slot extending therethrough and a plurality of retention slots disposed therein. Each retention slot includes a fastener disposed therein and each cartridge half further includes a plurality of pushers disposed therein in operative communication with the longitudinal slot and the plurality of retention slots. The cartridge assembly further includes a plurality of drive bars configured for translation through the cartridge assembly. Each drive bar is configured to translate through the longitudinal slot of one of the cartridge halves, whereby upon distal translation of one of the plurality of drive bars through the longitudinal slot of one of the cartridges halves, the one of the plurality of drive bars individually engages each pusher of the respective cartridge half to drive each pusher to sequentially eject the fastener from the associated retention slot.

Any of the above aspects of the present disclosure described may be combined with any other aspect of the present disclosure without departing from the scope of the present disclosure.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 13 is a top down view of the firing cam assembly of the cartridge assembly of FIG. 11;

FIG. 14 is a perspective view of the firing cam assembly of FIG. 13;

FIGS. 17-19 are enlarged cross-sectional views of the cartridge assembly of FIG. 4 indicated by the areas of detail 17, 18, 19 in FIG. 4, illustrating the firing and re-loading of a retention slot.

DETAILED DESCRIPTION OF EMBODIMENTS

Embodiments of the presently disclosed surgical stapling apparatus will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
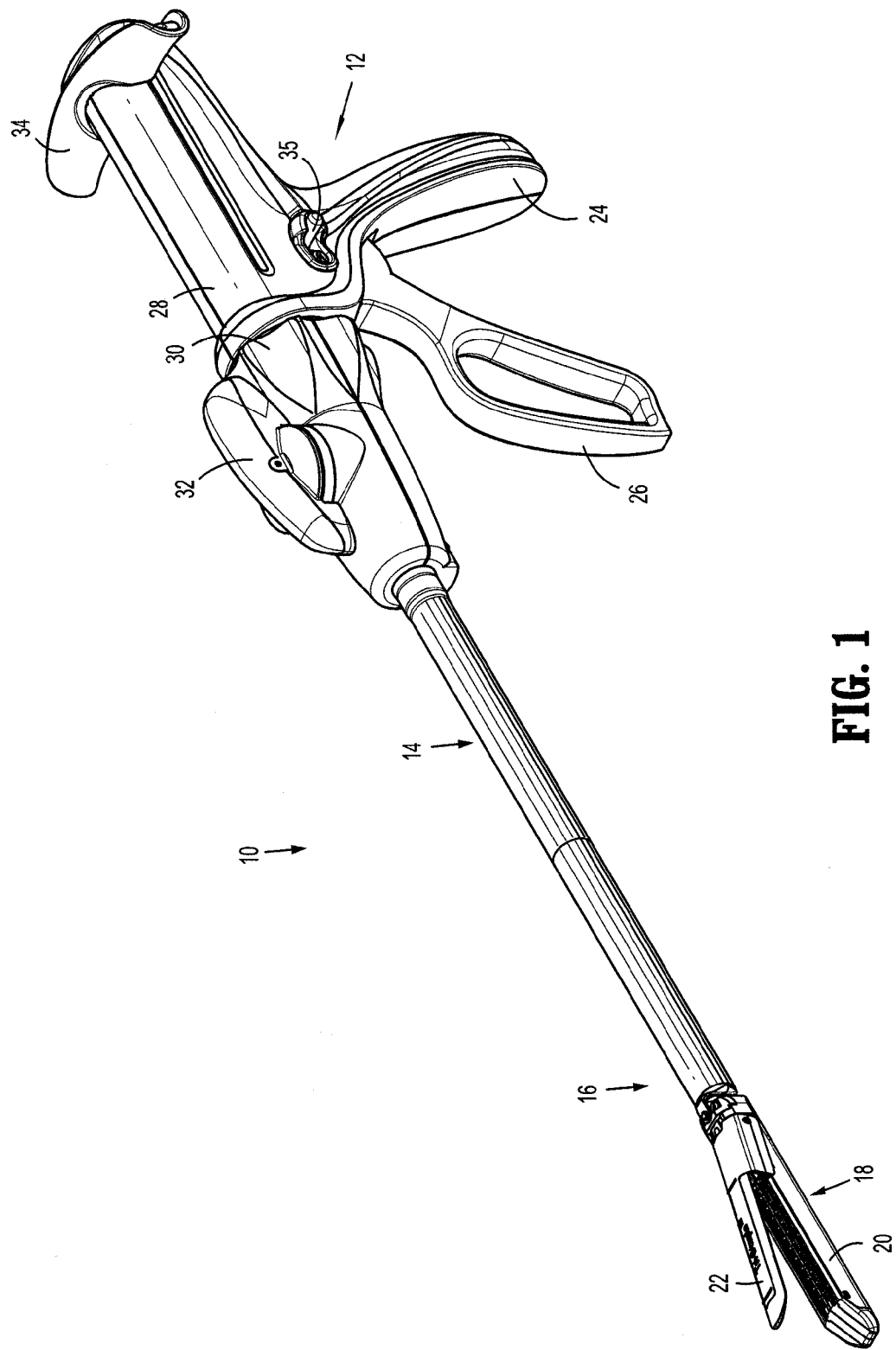
FIG. 1 is a perspective view of an exemplary surgical stapling apparatus according to the present disclosure.
Figure 2:
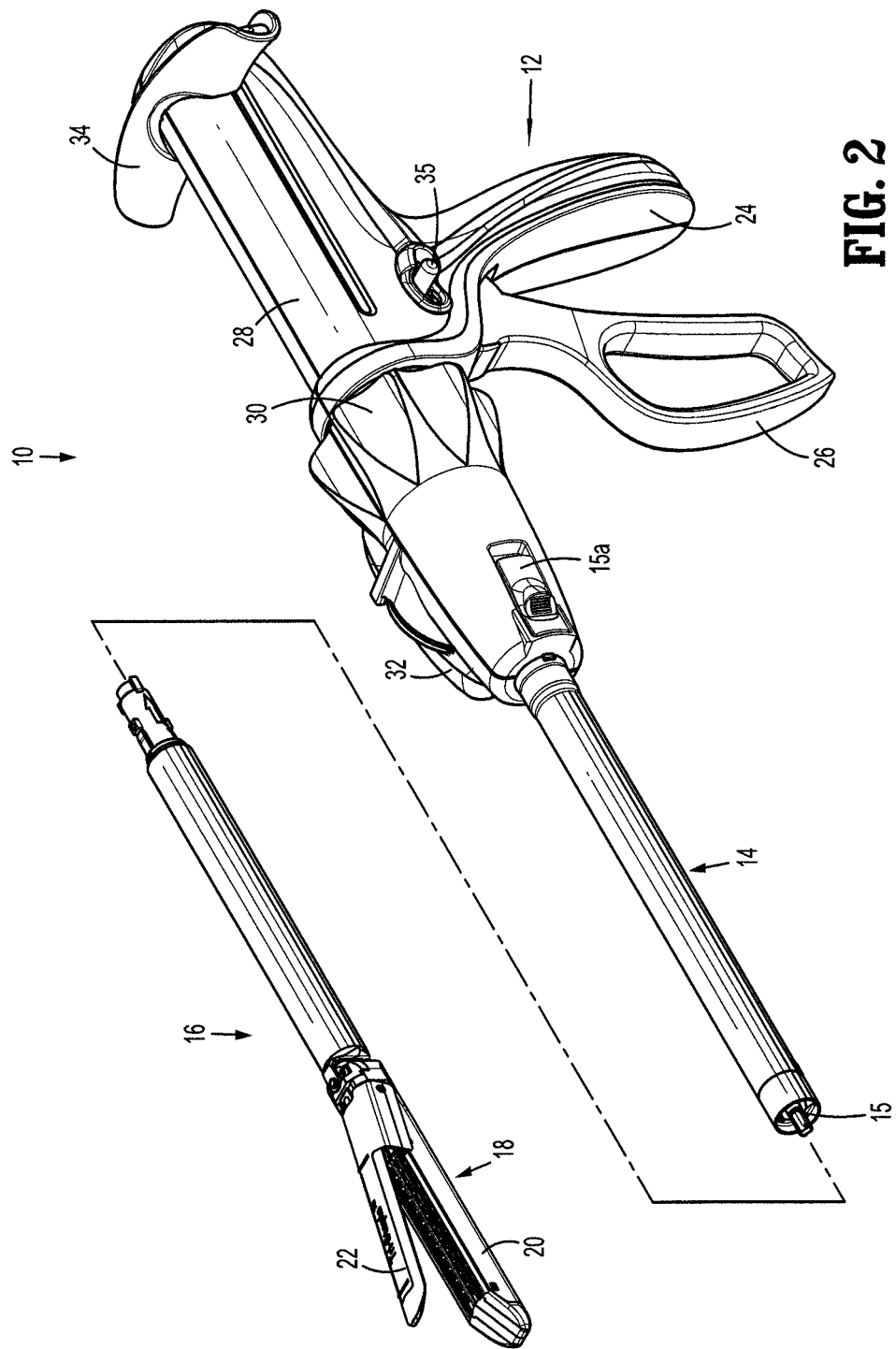
FIG. 2 is a perspective view of the surgical stapling apparatus of FIG. 1 with the disposable loading unit detached and the shaft rotated 90°.

FIGS. 1-2 illustrate one embodiment of the presently disclosed surgical stapling apparatus shown generally as 10. Briefly, surgical stapling apparatus 10 includes a handle assembly 12 and an elongated body 14. A loading unit or DLU 16 is releasably secured to a distal end of elongated body 14. loading unit 16 includes a tool assembly 18 having a cartridge assembly 20 housing a plurality of surgical staples and an anvil assembly 22 pivotably coupled in relation to cartridge assembly 20. A detailed description of the function of handle assembly 12, elongated body 14 and similar features of the loading unit 16 are disclosed in U.S. Pat. No 8,070,033 to Milliman et al. the entire contents of which are incorporated herein by reference. Once the surgical stapling apparatus 10 has been fired, the practitioner may remove the DLU 16, as described hereinabove, and install a new DLU 16.

Handle assembly 12 includes a stationary handle member 24, a movable handle member 26, and a barrel portion 28. Movable handle member 26 is operably coupled to loading unit 16 such that upon actuation of movable handle member 26, e.g., relative to stationary handle member 24, loading unit 16 is also actuated to grasp tissue and/or to fire and form fasteners through the grasped tissue.

A rotatable member 30 is preferably mounted on the forward end of barrel portion 28 to facilitate rotation of elongated body 14 with respect to handle assembly 12. For example, upon actuation, e.g. rotation, of rotatable member 30, elongated body 14 and loading unit 16 are also rotated. Rotatable member 30 may be rotated, for example, up to 180° in each direction.

Referring now to FIG. 2, with rotatable member 30 rotated 90°, a coupling mechanism 15 is shown. Coupling mechanism 15 is operably associated with elongated body 14 and loading unit 16 and is configured to control the coupling therebetween when loading unit 16 is coupled to elongated body 14. Loading unit 16 may be coupled to elongated body 14 by a coupling mechanism 15 such as a bayonet coupling, a snap fit coupling, or a similar coupling and may be secured in place by coupling mechanism 15. A release switch 15a is operatively associated with coupling mechanism 15 and is configured to release or decouple loading unit 16 from elongated body 14. In this manner, a used loading unit 16 may be removed and a new loading unit 16 may be coupled to elongated body 14.

An articulation lever 32 is also preferably mounted on the forward end of barrel portion 28 adjacent rotatable member 30 to facilitate articulation of tool assembly 18. For example, upon actuation of articulation lever 32 in a first direction, tool assembly 18 may also articulate in the first direction, and upon actuation of articulation lever 32 in a second direction, tool assembly 18 may also articulate in the second direction. It is also contemplated that tool assembly 18 may articulate in a direction opposite to the direction that articulation lever 32 is actuated.

A retraction member 34 is movably positioned along barrel portion 28 and operatively associated with tool assembly 18. Retraction member 34 is actuatable to return surgical stapling apparatus 10 to a retracted, or pre-fired, position. During operation, as movable handle member 26 is actuated to fire the surgical stapling device, retraction member 32 is translated distally. The position of retraction member 34 is maintained in place by a locking mechanism (not shown). A release button 35 is provided for temporarily deactivating this locking mechanism. Upon actuation of release button 35, retraction member 34 is no longer locked in place.

Figure 3:
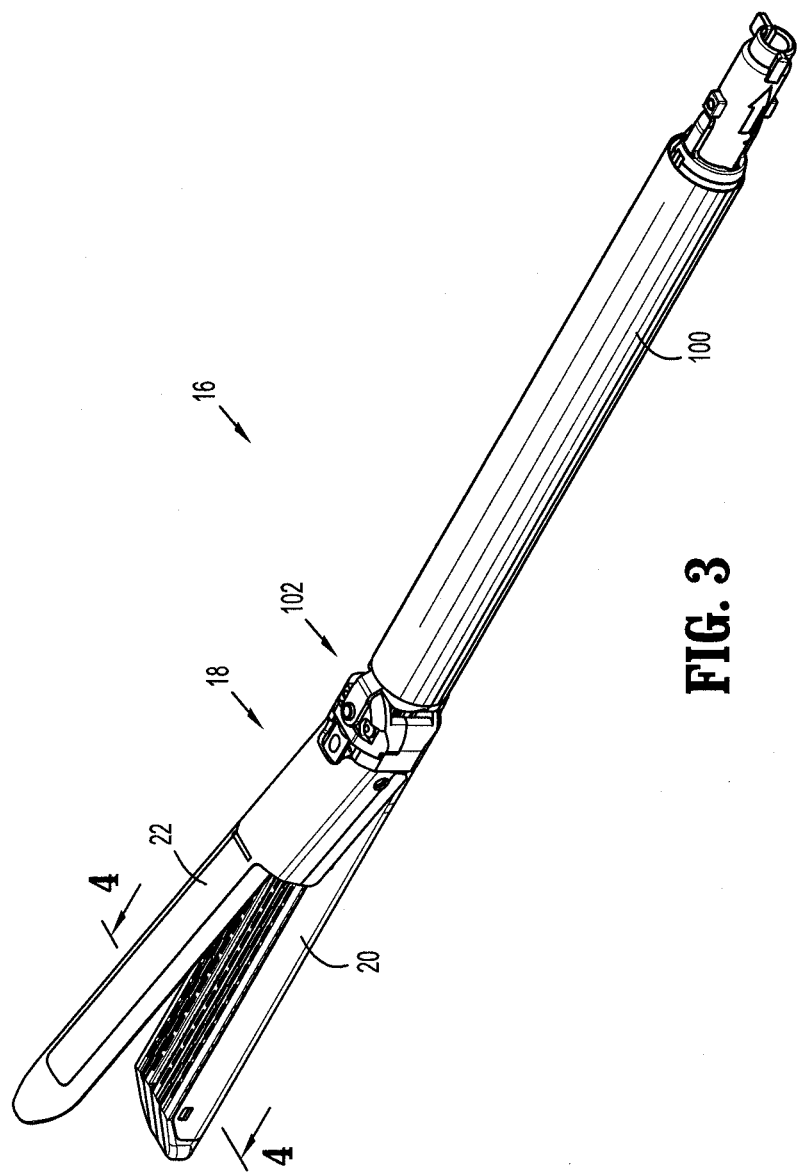
FIG. 3 a perspective view of the disposable loading unit of the surgical stapling apparatus of FIG. 1.

Referring to FIG. 3, loading unit 16 includes a proximal housing portion 100 adapted to releasably engage the distal end of body portion 14 (FIGS. 1 and 2). A mounting assembly 102 is pivotally secured to the distal end of housing portion 100, and is configured to receive the proximal end of tool assembly 18 such that pivotal movement of mounting assembly 102 about an axis perpendicular to the longitudinal axis of housing portion 100 effects articulation of tool assembly 18.

Figure 5:
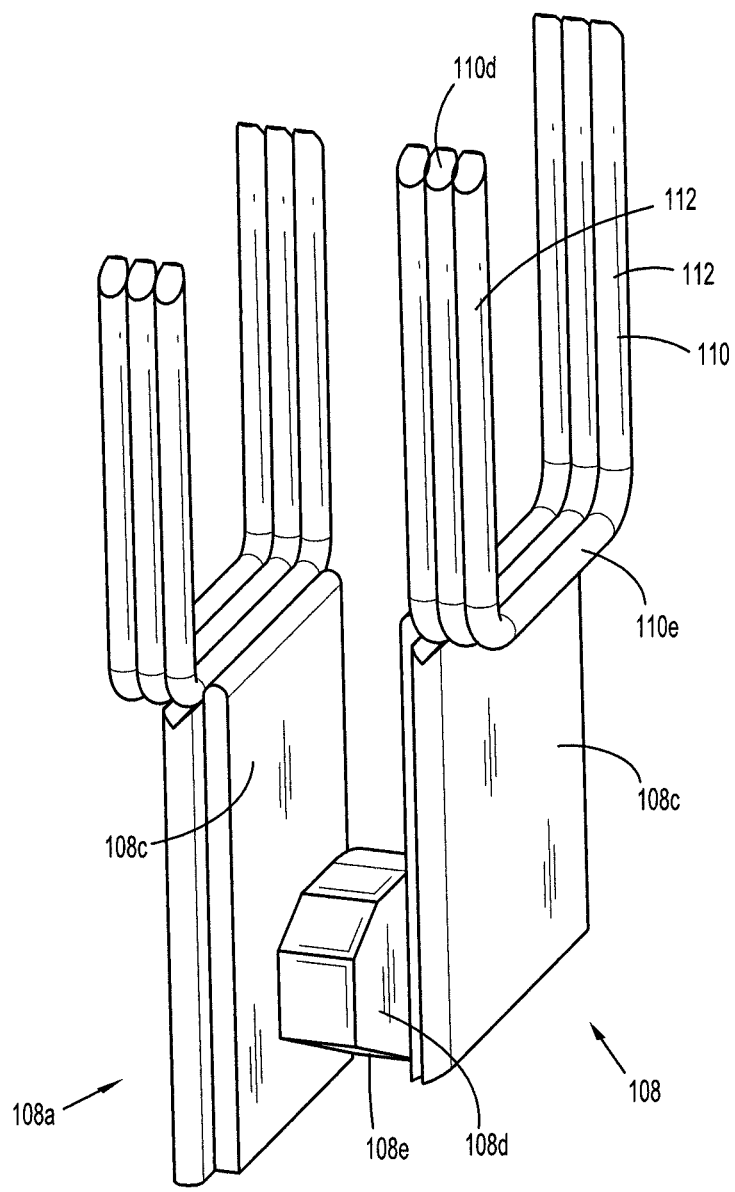
FIG. 5 is a perspective view of a two plate pusher in accordance with the present disclosure.
Figure 6:
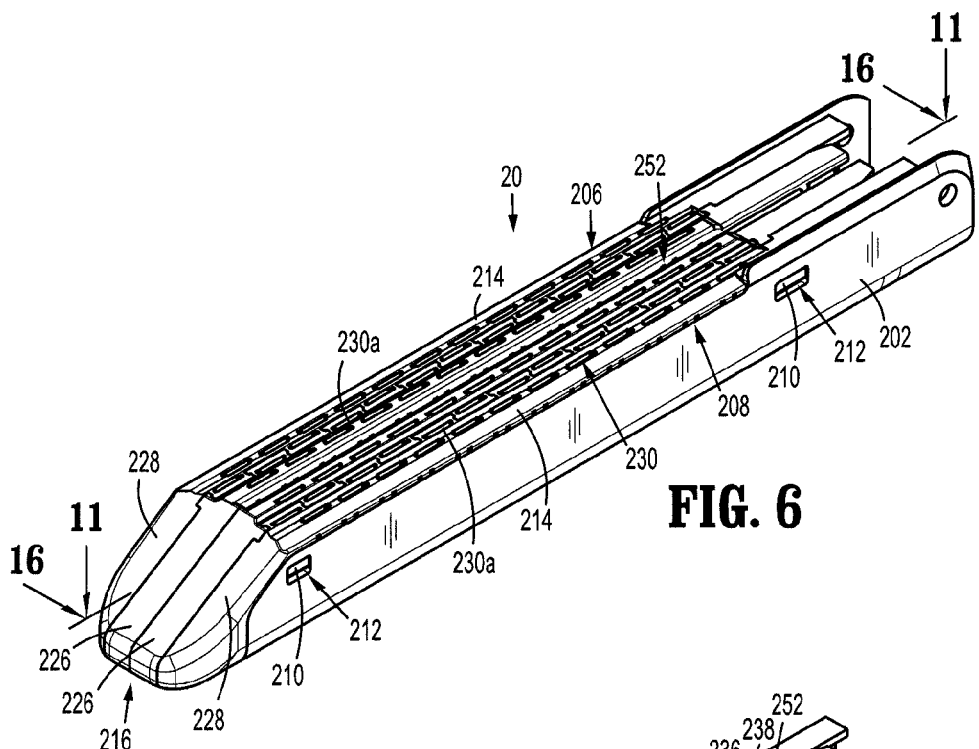
FIG. 6 is a perspective view of the cartridge assembly of the disposable loading unit of FIG. 3.
Figure 7:
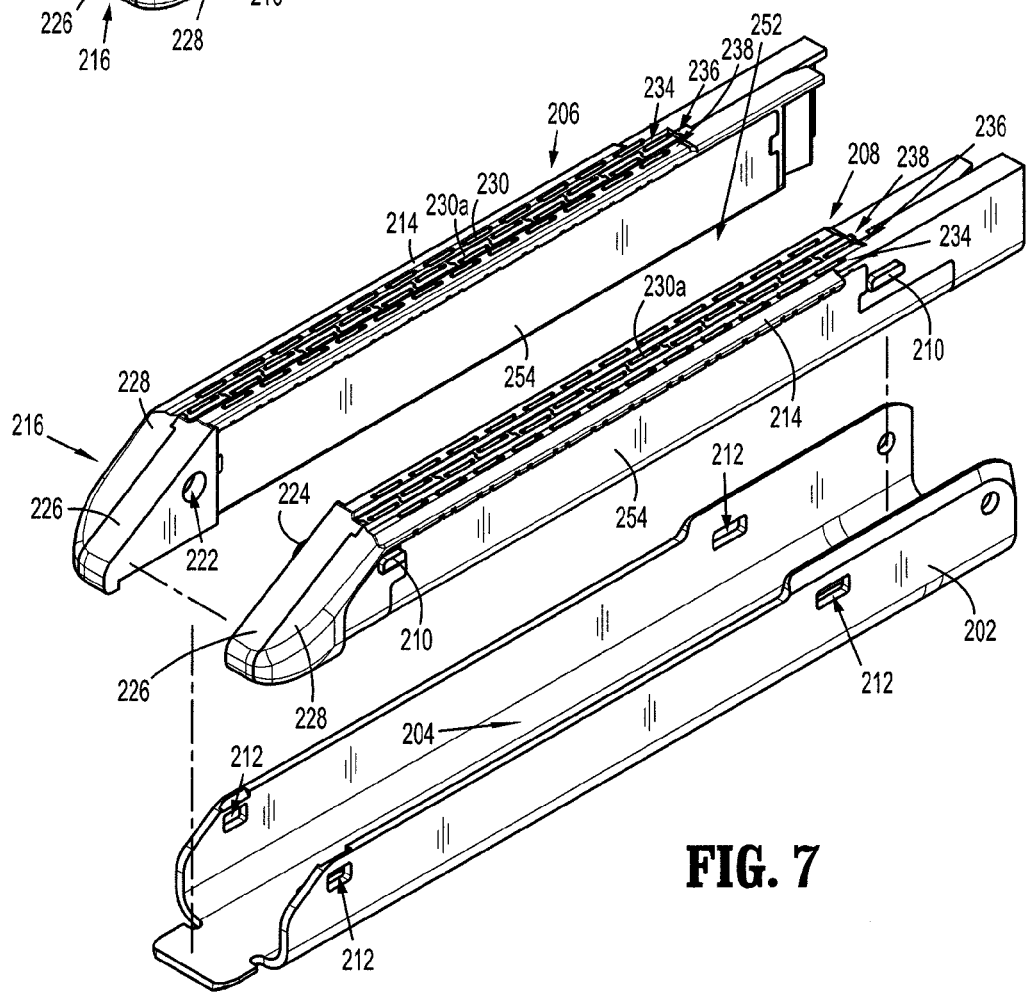
FIG. 7 is a exploded view of the cartridge assembly of FIG. 6, illustrating a pair of cartridges and a carrier.

Referring to FIGS. 3-10, tool assembly 18 preferably includes cartridge assembly 20 and anvil assembly 22 having staple forming pockets 22a (FIG. 18) disposed thereon. An example of a suitable anvil assembly 22 is disclosed in U.S. Pat. No. 5,865,361 to Milliman et al., referenced above. Cartridge assembly 20 includes a carrier 202 which defines an elongated support channel 204 (FIG. 7). Elongated support channel 204 is dimensioned and configured to receive a pair of staple cartridges 206, 208. Corresponding tabs 210 and slots 212 formed along staple cartridges 206, 208 and elongated support channel 204, respectively, function to retain staple cartridges 206, 208 within support channel 204. A support strut 214 formed along each staple cartridge 206, 208 is positioned to rest on a side wall of carrier 202 to further stabilize staple cartridges 206, 208 within support channel 204.

With reference now to FIGS. 6 and 7, staple cartridges 206, 208 are configured to couple together at a distal end portion 216 and define a central longitudinal slot 252 therebetween to facilitate passage of knife assembly 308 (FIG. 14) therethrough. An inner hole 222 formed on a surface of the distal end portion 216 of one of staple cartridges 206, 208 is configured to receive an inner tab 224 formed on a surface of the distal end portion 216 of the other of staple cartridges 206, 208. Inner hole 222 and inner tab 224 function to align staple cartridges 206, 208 when coupled together. Inner hole 222 and inner tab 224 in conjunction with tabs 210, slots 212, and struts 214 also function to maintain staple cartridges 206, 208 in a longitudinally fixed relation when inserted into elongated support channel 204 of carrier 202.

Figure 8:
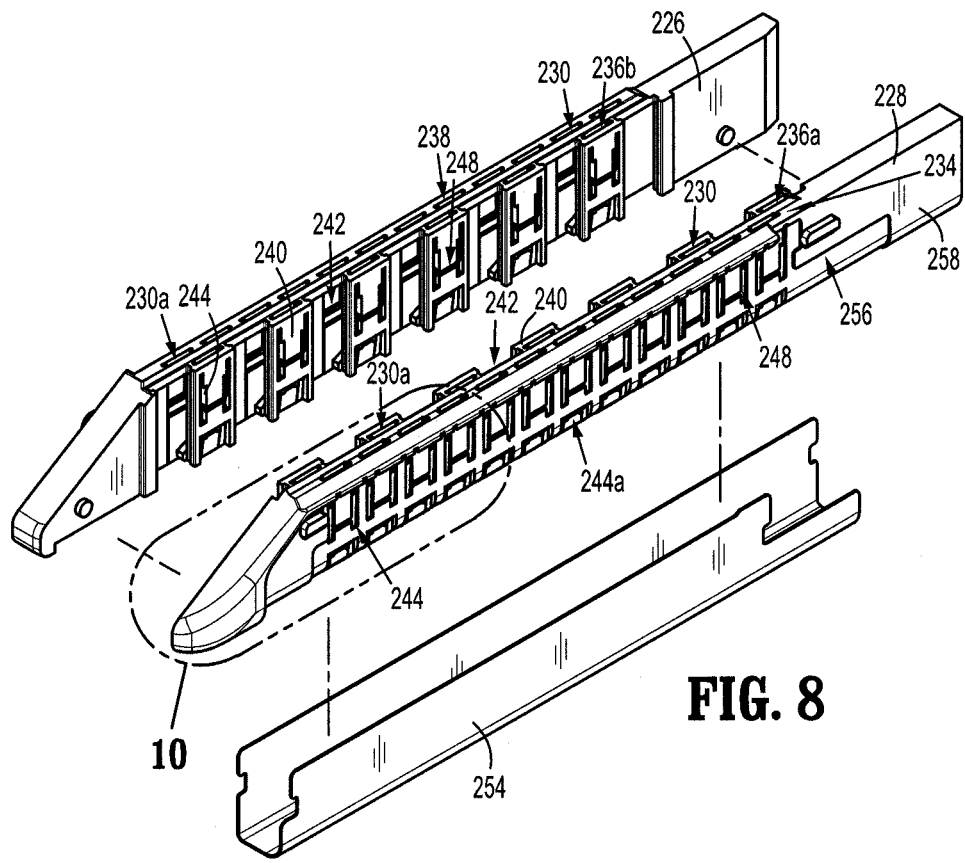
FIG. 8 is an exploded view of one of the cartridges of FIG. 7, illustrating two cartridge halves and a cartridge support channel.

With reference now to FIG. 8, each staple cartridge 206, 208 includes an inner half 226 and an outer half 228 configured to engage and couple to inner half 226. Each half 226, 228 includes retention slots 230 formed therein for receiving a plurality of fasteners 110 and pushers 108. Each fasteners 110 includes a pair of legs 112 having tips 110d and a backspan 110e. Retention slots 230 are aligned in rows, so that when inner half 226 and outer half 228 are coupled together, for example, three rows of retention slots 230 are defined. It is contemplated that cartridge halves 226, 228 may include fewer rows or additional rows of retention slots.

Outer half 228 includes a first row 234 of retention slots 230 and at least a portion 236a of a second row 236 of retention slots 230. Inner half 226 includes a third row 238 and at least a remaining portion 236b of the second row 236 of retention slots 230. When outer half 228 and inner half 226 are coupled together, the second row 236 of retention slots 230 is defined by the combination of portions 236a and 236b. For example, portions 236a and 236b may alternately define retention slots 230 of second row 236 as illustrated in FIG. 8.

Each of inner half 226 and outer half 228 includes a plurality of flanges 240 and a plurality of channels 242. Channels 242 are configured to receive flanges 240 during coupling of inner half 226 to outer half 228 such that the channels 242 of each of inner and outer halves 226, 228 match up with the flanges 240 of the other of inner and outer halves 226, 228 when the inner and outer halves 226, 228 are joined together. Channels 242 and flanges 240 may alternate along the length of each of inner half 226 and outer half 228, as illustrated in FIG. 8. Each flange 240 includes one of retention slots 230 of second row 236. Retention slots 230 of flanges 240 may be configured such that when inner half 226 and outer half 228 are coupled together, flanges 240, and the retention slots 230 disposed therein, are substantially longitudinally aligned to form second row 236. Alternatively, retention slots 230 of flanges 240 of each of inner and outer halves 226 and 228 may be slightly offset from a longitudinal axis such that retention slots 230 of flanges 240 of respective inner and outer halves 226 and 228 are not substantially longitudinally aligned.

Referring now to FIGS. 4 and 6-8, each cartridge 206, 208 includes a cartridge support channel 254 dimensioned and configured to receive inner and outer halves 226 and 228. Cartridge support channel 254 is configured to maintain inner and outer halves 226 and 228 in engagement in longitudinal alignment with one another. Inner and outer halves 226 and 228 include recessed sections 256 dimensioned and configured for receiving cartridge support channel 254 such that cartridge support channel 254 is substantially aligned with side surfaces 258 of inner and outer halves 226 and 228. This assists in maintaining inner and outer halves 226, 228 coupled together without adding additional width to each cartridge 206, 208 thereby maintaining a minimal width of the overall cartridge assembly 20.

Figure 4:
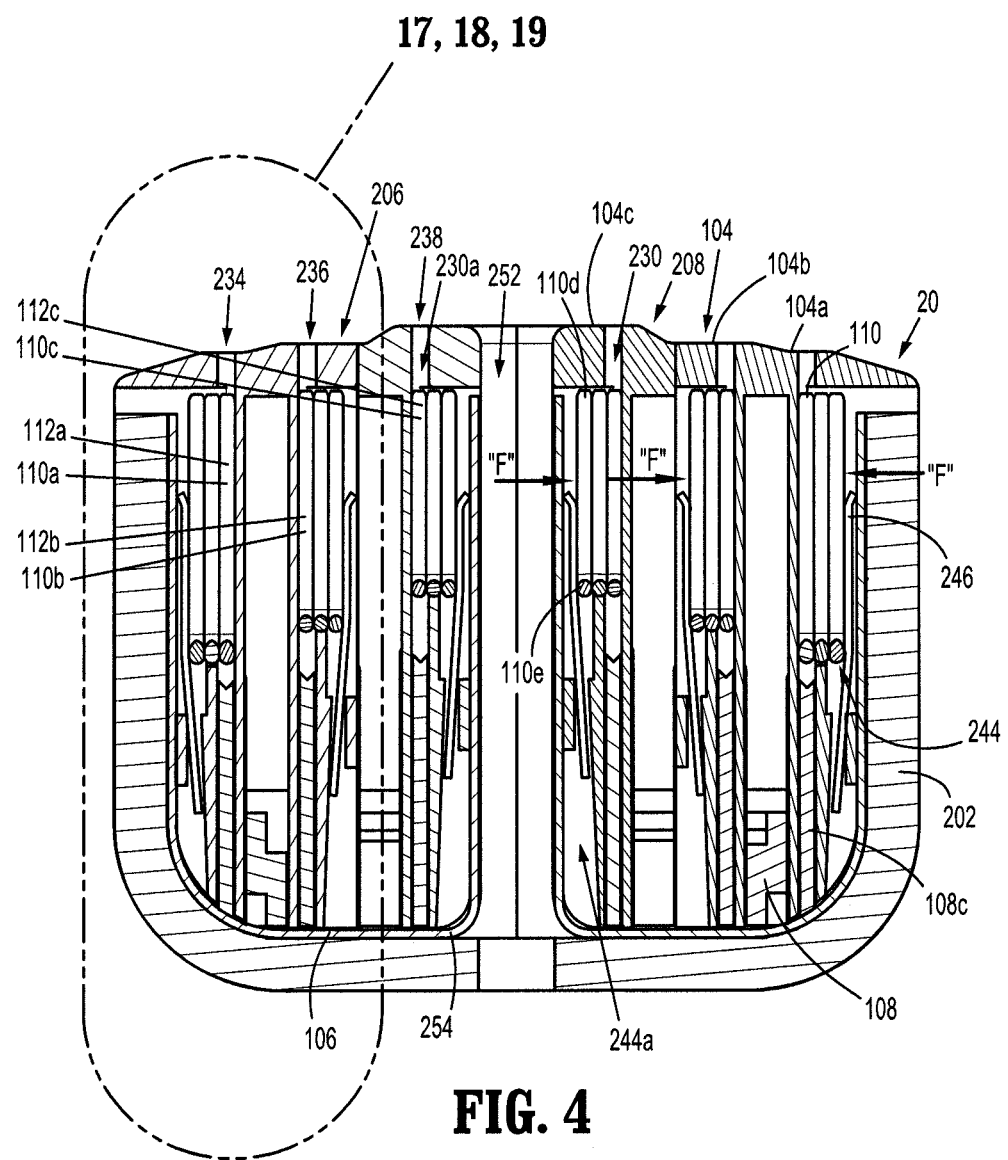
FIG. 4 is a cross-sectional view of the disposable loading unit of FIG. 3 taken along section line 4-4.

Referring now to FIG. 4, in any of the embodiments disclosed herein, one or more of the cartridges 206, 208 includes a tissue contacting surface 104 that is stepped. For example, an outer tissue contacting surface 104a, an intermediate tissue contacting surface 104b, and an inner tissue contacting surface 104c form a stepped configuration. Each tissue contacting surface 104a-104c has a different height from one another as measured from a bottom surface 106 of a respective cartridge 206, 208. Specifically, tissue contacting surfaces 104a-104c are planar structures that are substantially parallel to one another, but are not co-planar (i.e. stepped) with one another. In addition, each tissue contacting surface 104a-c defines a planar axis that extends through the respective tissue contacting surface 104a-c. A first wall surface interconnects tissue contacting surfaces 104a and 104b, while a second wall surface interconnects tissue contacting surfaces 104b and 104c. The first and second wall surfaces are planar structures wherein each wall surface defines a planar axis. In one embodiment, the planar axes of the wall surfaces are orthogonal to the planar axes of tissue contacting surfaces 104a-c. In one embodiment, inner tissue contacting surface 104c is defined on inner half 226 of each cartridge 206, 208, outer tissue contacting surface 104a is defined on outer half 228 of cartridge, and intermediate tissue contacting surface 104b is defined by the joining of inner half 226 and outer half 228 when inner and outer halves 226, 228 are coupled together.

Inner tissue contacting surface 104c has the greatest height, outer tissue contacting surface 104a has the least height, and intermediate tissue contacting surface 104b has a height between the heights of outer and inner tissue contacting surfaces 104a, 104c (see FIG. 4). While tissue contacting surfaces 104a-104c are shown as increasing in height from outer most tissue contacting surface 104a to inner most tissue contacting surface 104c, it is within the scope of the present disclosure that the heights of each tissue contacting surface can vary depending on the particular surgical procedure. For example, tissue contacting surfaces 104a-104c can increase in height from the inner most tissue contacting surface 104c to the outer most tissue contacting surface 104a, the intermediate tissue contacting surface 104b can have the greatest height, the intermediate tissue contacting surface 104b can have the least height, or at least two of tissue contacting surfaces 104a-104c can have the same height.

As seen in FIG. 4, each row 234, 236, 238 may include fasteners 110 having different sizes. For example, legs 112a of surgical fasteners 110a disposed in retention slots 230 of first row 234 may have a first leg length, legs 112b of surgical fasteners 110b disposed in retention slot 230 of second row 236 may have a second leg length, and legs 112c of surgical fasteners 110c disposed in retention slot 230 of third row 238 may have a third leg length. In particular, surgical fasteners 110a-110c increase in height from the inner most row 238 to the outermost row 234 of each cartridge. In one embodiment, legs 112c of surgical fasteners 110c have a leg length of about 2.3 mm, legs 112b of surgical fasteners 110b have a leg length of about 3.5 mm, and legs 112a of surgical fasteners 110a have a leg length of about 4.1 mm. As such, inner tissue contacting surface 104c has the greatest height and retains surgical fasteners 110c having the shortest leg lengths, and outer tissue contacting surface 104a has the least height and retains surgical fasteners 110a having the longest leg lengths. Tissue contacting surface 104 step progressively downward at intermediate tissue contacting surface 104b and then again at outer tissue contacting surface 104a. It is envisioned and within the scope of the present disclosure that any number of arrangements are possible. In any of the embodiments disclosed herein, the cartridge or cartridges can include staples of different sizes or the cartridge or cartridges can have staples that are all the same size.

With reference now to FIGS. 4 and 8-10, each retention slot 230 of inner and outer halves 226 and 228 has a staple magazine 244 operatively associated therewith. The staple magazine is positioned in a flange 240. Each staple magazine 244 includes a plurality of fasteners 110 disposed therein and a biasing member 246 configured to bias and urge the plurality of fasteners 110 towards the respective retention slot 230. As discussed above, retention slots 230 that are disposed on different rows 234, 236 and 238 may include fasteners 110 having different sizes. It is further contemplated that each magazine 244 associated with an adjacent retention slot 230 includes a plurality of fasteners 110 having the same size as the fastener 110 disposed in the adjacent retention slot 230. For example, magazines 244 associated with retention slots 230 of first row 234 may include fasteners 110a have the first size, magazines 244 associated with retention slots 230 of second row 236 may include fasteners 110b have the second size, and magazines 244 associated with retention slots 230 of third row 238 may include fasteners 110c have the third size.

Figure 10:
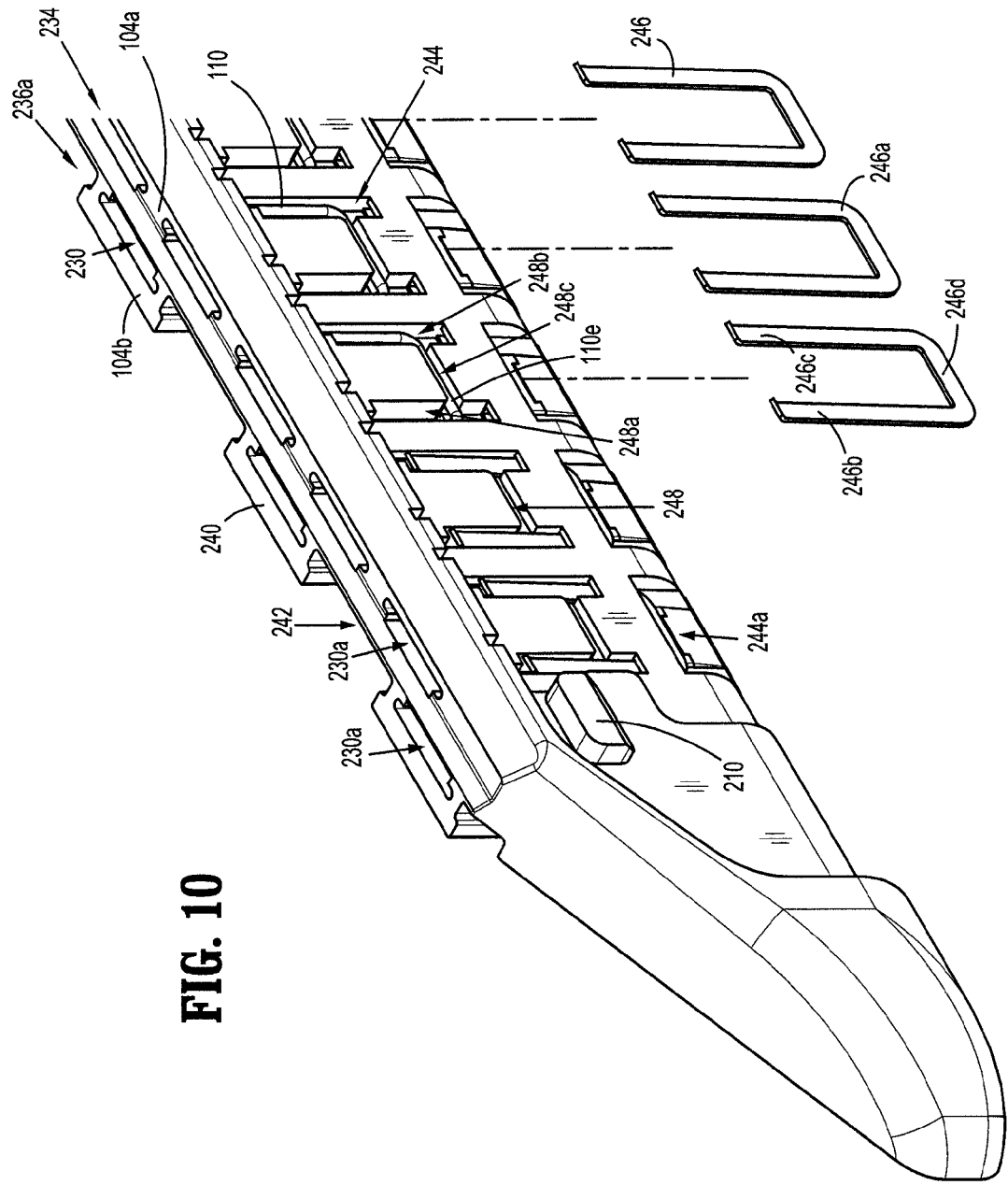
FIG. 10 is an enlarged, partially exploded, view of the distal end of one of the cartridge halves of FIG. 8 indicated by the area of detail 10.

Referring now to FIG. 10, staple magazine 244 generally defines a "U" or "H" shaped channel 248 for reception of fasteners 110 therein. Channel 248 includes a pair of vertical segments 248a, 248b and a horizontal segment 248c. With reference to FIG. 5, each fastener 110 disposed within channel 248 is maintained in a vertical orientation, with tips 110d oriented toward the tissue contacting surface 104 of the respective cartridge 206, 208, and aligned parallel to a plane defined by the fastener 110 disposed within the respective retention slot 230. For example, the backspan 110e of a fastener 110 disposed within channel 248 of magazine 244 rests on horizontal segment 248c and the legs 112 of the fastener 110 disposed within channel 248 are disposed within vertical segments 248a and 248b. This ensures that when a fastener 110 is loaded from a magazine 244 into a respective retention slot 230, the fastener 110 is properly oriented toward the tissue contacting surface 104 for firing.

Each magazine 244 includes at least one channel 244a for receiving at least a portion of biasing member 246 therethrough where biasing member 246 is configured to extend from the at least one channel 244a into at least one of vertical segments 248a and 248b adjacent the plurality of fasteners 110 disposed in magazine 244 to engage the plurality of fasteners 110 and urge the plurality of fasteners 110 towards the respective retention slot 230. It is contemplated that a separate biasing member 246 may extend into each vertical segment 248a and 248b. In an embodiment, biasing member 246 includes a pair of legs 246b, 246c, and a backspan 246d where the pair of legs 246b, 246c extends into vertical segments 248a, 248b, respectively when biasing member 246 is inserted into channel 244a of magazine 244.

With reference now to FIG. 4, legs 246b and 246c of biasing member 246 may define a slight curve such that when biasing member 246 is inserted into channel 244a of magazine 244 and engages the plurality of fasteners 110 disposed therein, legs 246b and 246c bias the plurality of fasteners 110 toward the respective retention slot 230 and in vertical registration with the respective retention slot 230. Biasing member 246 is inserted into channel 244a in a substantially vertical manner and upon encountering one in the plurality of fasteners 110, legs 246b and 246c are deflected outward and engage the plurality of fasteners with a biasing force "F". Biasing member 246 may be formed of any resilient or flexible material which resists deformation or applies a force to return to its pre-deformation state.

Biasing member 246 may be any suitable mechanism for biasing the plurality of fasteners 110 disposed in magazine 244 toward retention slot 230, as described above, including, for example, springs, resilient members, or other similar biasing elements. In one embodiment, biasing member 246 is a leaf spring 246a having a substantially "U" shape. It is contemplated that biasing member 246 may have other shapes suitable for use in biasing fasteners 110 disposed in magazine 244 toward retention slot 230.

With reference now to FIGS. 4, 5, 9, and 16-19, a plurality of pushers 108 are disposed within each of the inner and outer halves 226, 228 of cartridges 206, 208 and are operatively associated with the plurality of retention slots 230. Each pusher 108 includes a pusher plate 108c disposed within one of retention slots 230 and in operative association with the fastener 110 disposed within the respective retentions slot 230. Each pusher plate 108c is configured to translate through the respective retention slot 230 to urge the fastener 110 disposed therein out of the retention slot 230 through a respective opening 230a in tissue contacting surface 104, through tissue disposed between anvil assembly 22 and the cartridge assembly 20, and against staple forming pockets 22a (FIG. 18) of anvil assembly 22.

In one embodiment, as illustrated in FIG. 4, pusher plates 108c disposed in the retention slots 230 of first row 234 may have a first size, pusher plates 108c disposed in the retention slots 230 of second row 236 may have a second size, and pusher plates 108c disposed in retention slots 230 of third row 238 may have a third size. For example, pusher plates 108c of the first row 234 may be smaller than pusher plates 108c of second row 236, and pusher plates 108c of second row 236 may be smaller than pusher plates 108c of third row 238. Having pusher plates 108c with different sizes allows pusher plates 108c to accommodate fasteners 110a-110c having different sizes or allows pusher plates 108c to accommodate rows 234, 236, 238 having tissue contacting surfaces 104a-c of different heights. Pusher plates 108c of each pusher 108 may alternatively be the same size. A tray or other member may be provided to maintain the position of the pushers prior to the staple cartridge being installed in the cartridge support channel.

Figure 9:
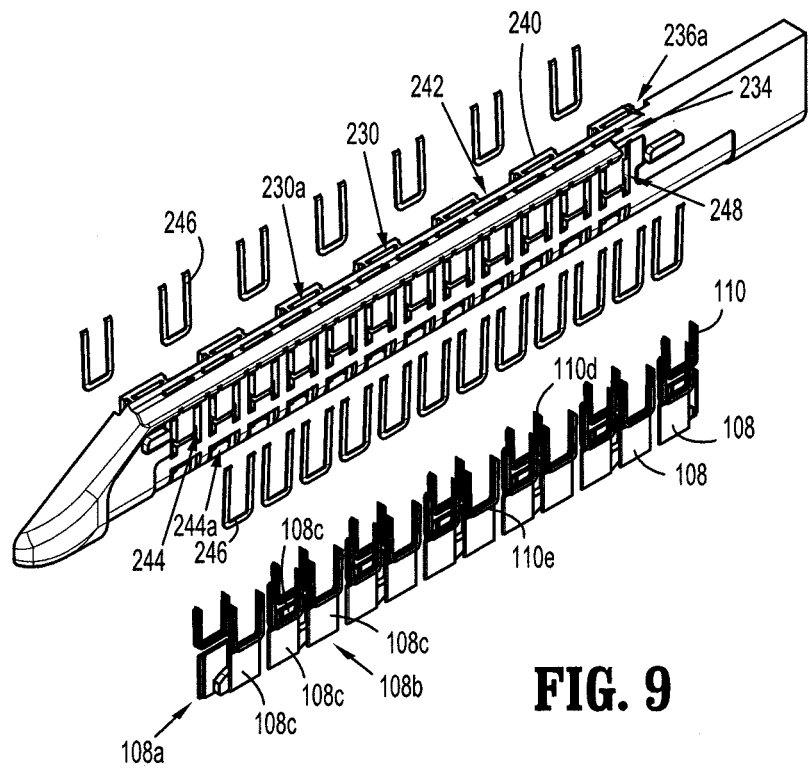
FIG. 9 is an exploded view of one of the cartridge halves of FIG. 8, illustrating the pushers, biasing members and fasteners removed.

Each pusher 108 may be operatively associated with one or more retention slots 230 such that upon actuation thereof, pusher 108 may fire one or more fasteners 110 out of retention slots 230 through openings 230a. For example, as illustrated in FIG. 5, a pusher 108a including two pusher plates 108c is configured to fire two fasteners 110. As illustrated in FIG. 9, cartridge halves 226, 228 may include more than one type of pusher where, for example, pushers 108a, including two pusher plates 108c, that are configured for operative association with two retention slots 230 may be disposed at either end of the respective row 234, 236, 238, and pushers 108b, including three pusher plates 108c, that are configured for operative association with three retention slots 230 may be disposed between the ends of the respective rows 234, 236, 238. It is contemplated that alternate arrangements are possible where two and three retention slot pushers 108a, 108b may be included in any order. Alternatively, only one type of pusher 108 may be used, e.g., only pushers 108a configured for use with two retention slots or only pushers 108b configured for use with three retention slots. In this manner, each retention slot 230 is operatively associated with a pusher 108 that is configured to fire a fastener 110 disposed therein. It is alternatively contemplated that each pusher 108 may only include one pusher plate 108c and may only be associated with a single retention slot 230 or that each pusher 108 may include a plurality of pusher plates 108c configured for use with a plurality of retention slots 230.

Referring now to FIGS. 17-19, during firing, as a pusher plate 108c translates through a corresponding retention slot 230 to a fired position, pusher plate 108c at least partially blocks or covers an opening 232 between retention slot 230 and magazine 244 to inhibit reloading of retention slot 230 with a new fastener 110 by magazine 244 until the firing stroke is complete. As pusher plate 108c returns to its pre-fired position at the base of retention slot 230, opening 232 is uncovered or opened to magazine 244 and receives the next fastener 110 from magazine 244 due to biasing force "F" of biasing member 246. It is contemplated that the next fastener 110 from magazine 244 may be at least partially received through opening 232 and within retention slot 230 as pusher plate 108c returns toward its pre-fired position where, for example, tips 110d of the next fastener 110 may be received through opening 232 and within retention slot 230 before backspan 110e is received through opening 232 and within retention slot 230.

Referring now to FIGS. 11-19, a firing cam assembly 300 is disposed at least partially within proximal housing 100 of loading unit 16 and extends at least partially into tool assembly 18. Firing cam assembly 300 is disposed in operative communication with handle assembly 12 and is configured to translate distally and proximally through tool assembly 18 upon actuation of handle assembly 12, as will be described below in more detail.

Figure 4A:
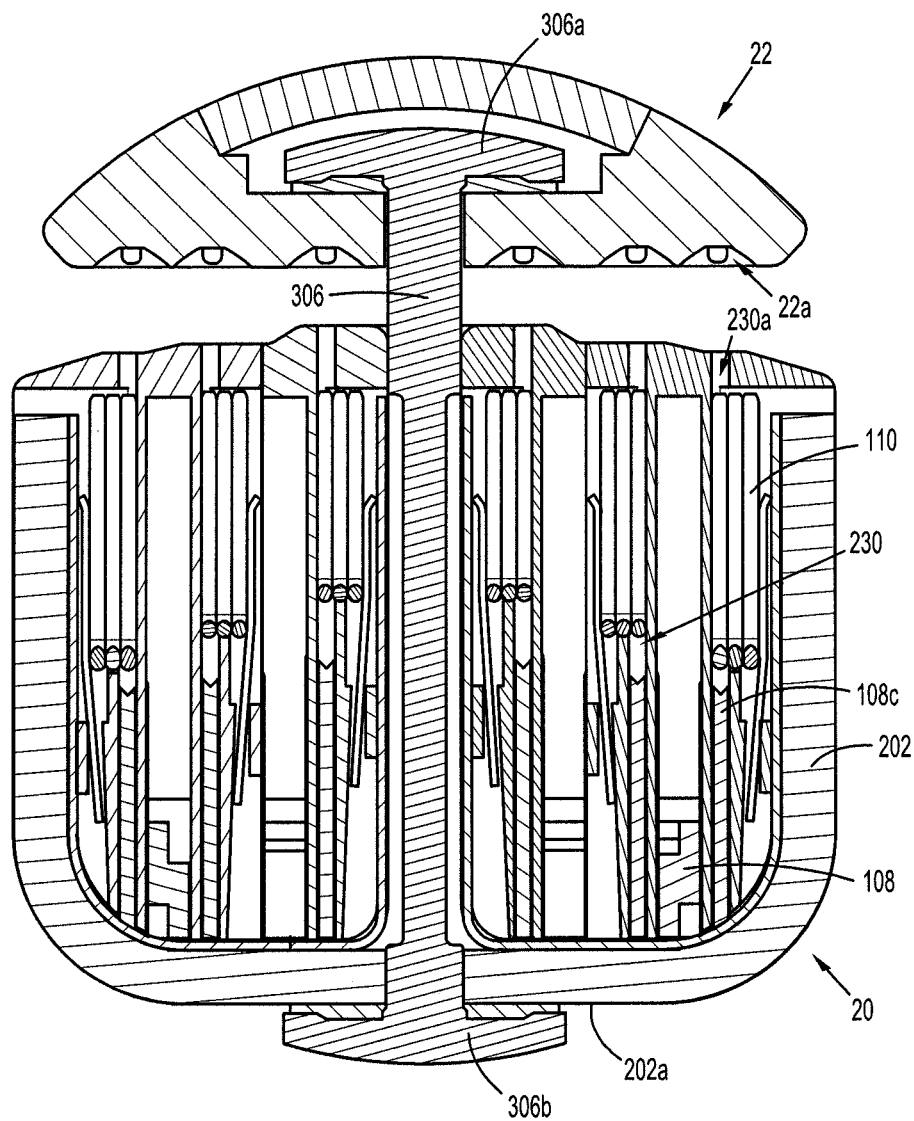
FIG. 4a is a cross-sectional view of the disposable loading unit of FIG. 3 taken along section line 4-4, illustrating the knife assembly disposed in the central channel and an anvil assembly.
Figure 15:
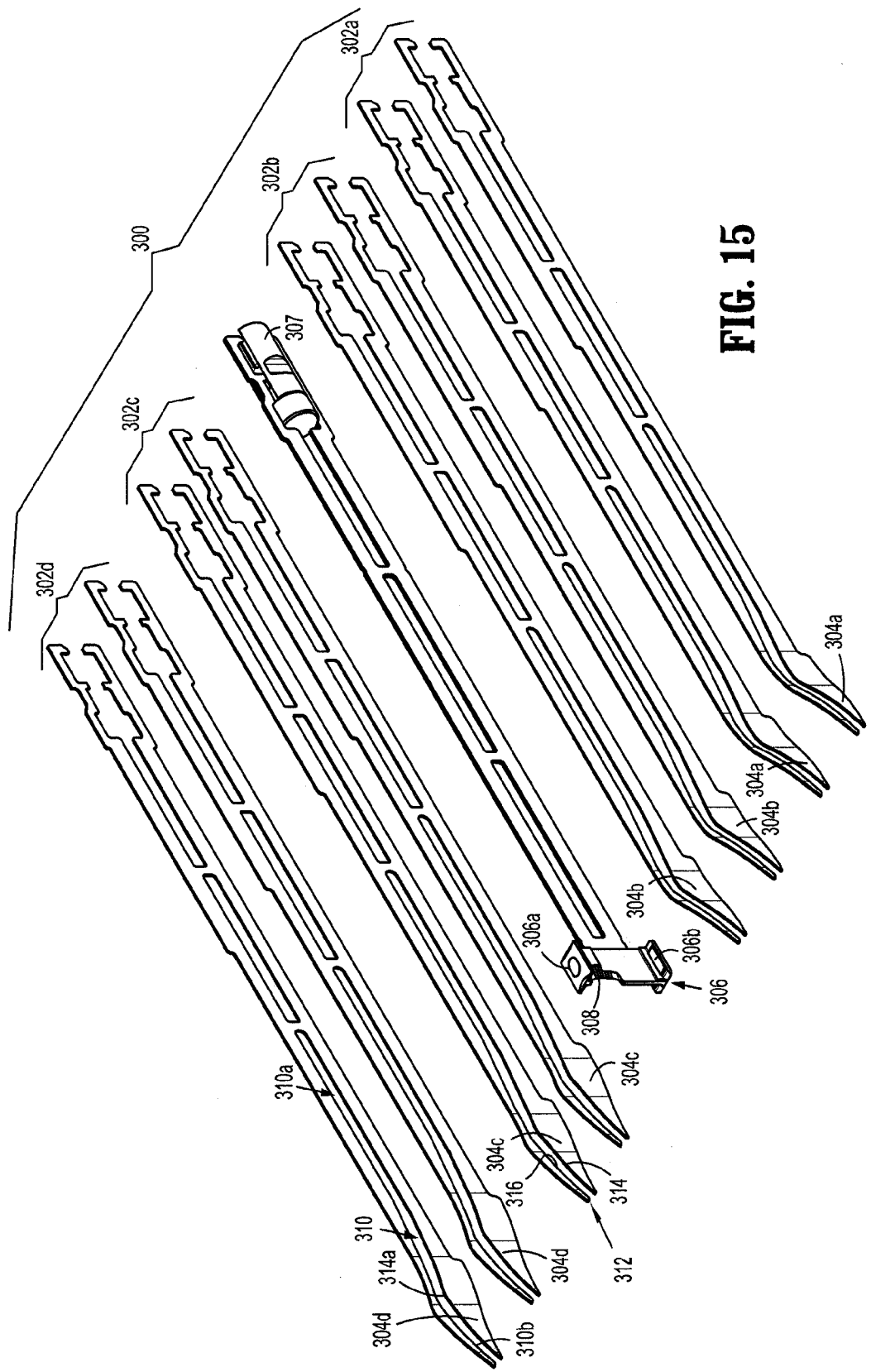
FIG. 15 is an exploded view of the firing cam assembly of FIG. 14.

With reference now to FIGS. 13-15, firing cam assembly 300 includes a plurality of drive bars 302 having firing cams 304 disposed at a distal end thereof and a central drive member 306 having a knife assembly 308 disposed at a distal end thereof. Knife assembly 308 defines a substantially I-shaped cross section having a top flange 306a, a bottom flange 308b and a knife blade 308c. As discussed above, a central longitudinal slot 252 extends along the length of cartridge assembly 20 between staple cartridges 206, 208 to facilitate passage of central drive member 306 and knife assembly 308 therethrough. With reference now to FIG. 4A, top flange 308a is configured to translate through a longitudinal slot 22b of anvil assembly 22 and bottom flange 308b is configured to translate longitudinally along an underside 202a of carrier 202.

Figure 11:
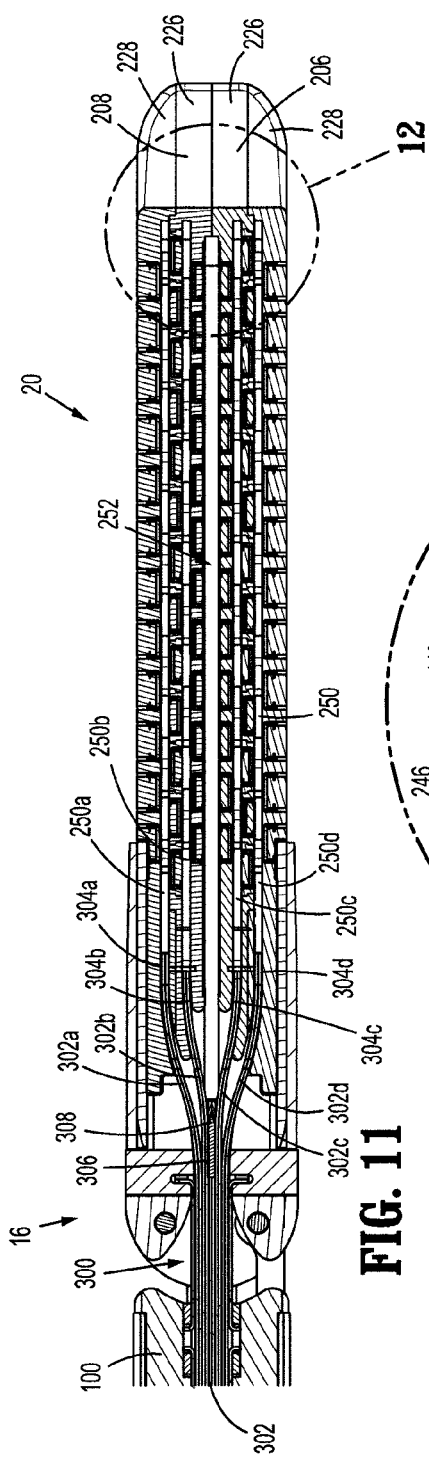
FIG. 11 is a cross-sectional view of the cartridge assembly of FIG. 6, taken along section line 11-11.
Figure 12:
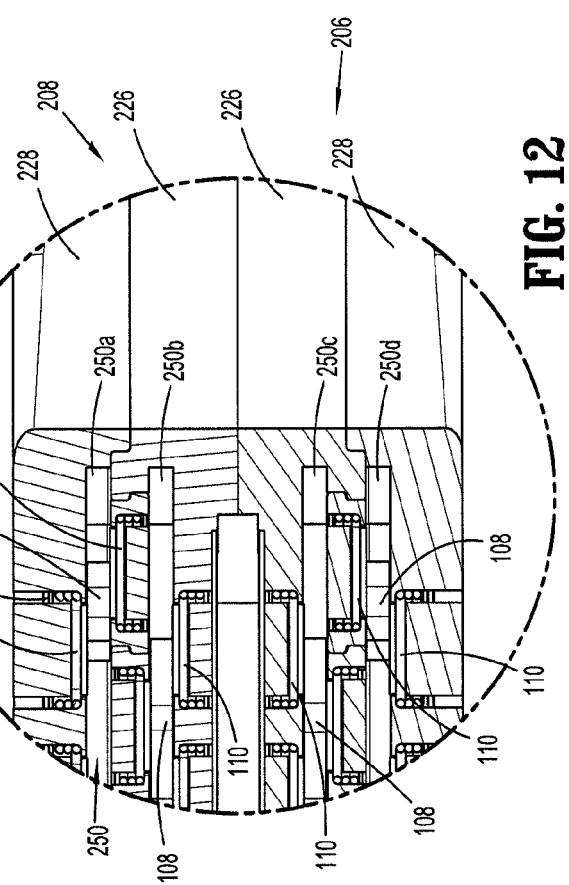
FIG. 12 is an enlarged view of the distal end portion of the cartridge assembly of FIG. 11 indicated by the area of detail 12.

With reference now to FIG. 11, each half 226, 228 of each cartridge 206, 208 includes a longitudinal slot 250 extending at least partially therethrough to accommodate passage of at least one of drive bars 302 and firing cams 304 of firing cam assembly 300 therethrough. It is contemplated, for example, that each slot 250 may accommodate passage of a single drive bar 302 and firing cam 304 or may accommodate passage of multiple drive bars 302 and firing cams 304.

With reference now to FIG. 4A, during operation of surgical stapling apparatus 10, as firing cam assembly 300 translates through loading unit 16, knife assembly 308 translates through longitudinal slot 250 with top flange 306a translating through longitudinal slot 22a of anvil assembly 22 and bottom flange 306b translating along underside 202a of carrier 202 to approximate anvil assembly 22 and cartridge assembly 20 together. As knife assembly 308 translates through slot 250, knife blade 308c severs the portion of tissue that is disposed between anvil assembly 22 and cartridge assembly 20 adjacent slot 250.

With reference now to FIGS. 11, 12 and 16-19, as firing cam assembly 300 translates through loading unit 16, drive bars 302 of firing cam assembly 300 translate through the longitudinal slots 250 of each half 226, 228 of each staple cartridge 206, 208. The Firing cams 304 are advanced into sequential contact with the pushers 108 associated with retention slots 230, to cause pusher plates 108c to translate vertically within retention slots 230 and urge fasteners 110 from retention slots 230 through openings 230a in tissue contacting surface 104, through tissue disposed between anvil assembly 22 and the cartridge assembly 20, and against staple forming pockets 22a of anvil assembly 22 for staple forming.

As illustrated in FIGS. 11, 13 and 14, drive bars 302 are initially disposed adjacent to one another within proximal housing 100 of loading unit 16 and are resilient or flexible such that they may spread out to translate through longitudinal slots 250.

Referring now to FIGS. 11 and 13-15, firing cam assembly 300 may include, for example, four pairs of drive bars 302a-302d including four pairs of corresponding firing cams 304a-304d. Each pair of drive bars 302a-302d corresponds to a respective longitudinal slot 250a-250d of cartridges 206, 208 and is translatable through the respective longitudinal slot 250a-250d to actuate pushers 108 disposed in the respective longitudinal slot 250a-250d to effect firing of fasteners 110 disposed in corresponding retention slots 230. Drive bars 302a-302d and central drive member 306 are coupled together at the proximal end by a retaining member 307.

Figure 16:
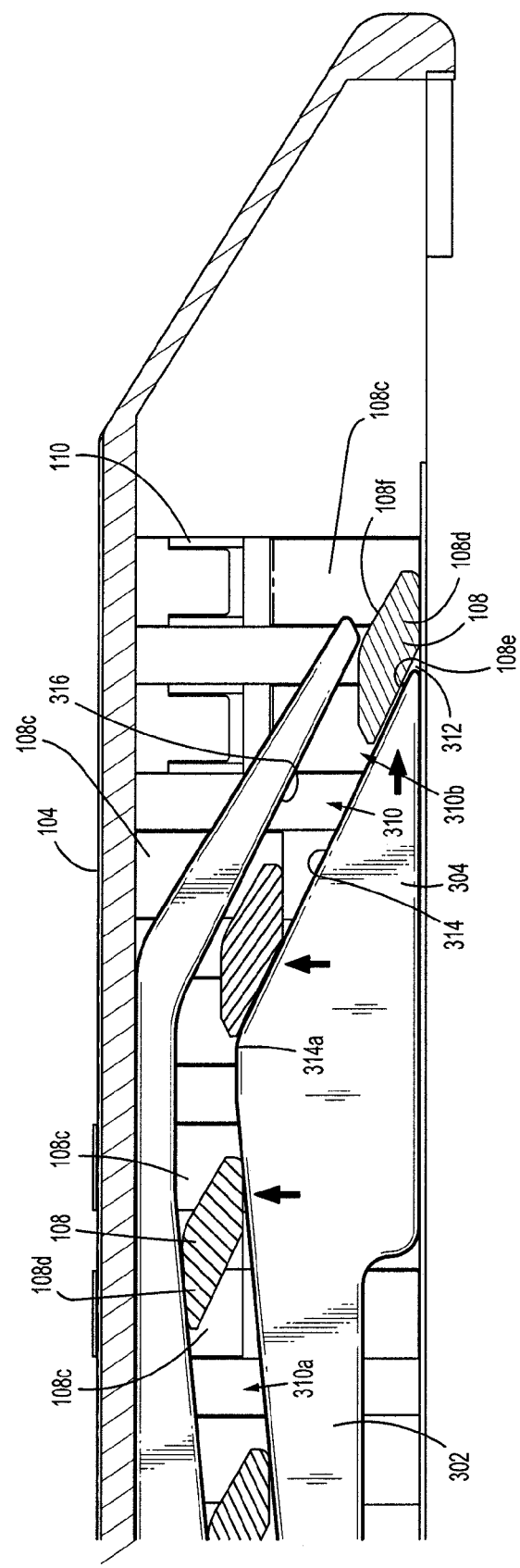
FIG. 16 is a side, cross-sectional view of the cartridge assembly of FIG. 6, taken along section line 16-16.

Referring now to FIGS. 5 and 16, each pusher 108 includes a pusher base 108d having a proximal cam surface 108e and a distal cam surface 108f. Each pusher base 108d is disposed within one of longitudinal slots 250 with the proximal and distal cam surfaces 108e, 108f being configured for engagement with at least one of firing cams 304 upon distal translation thereof to cause pusher 108 to translate toward tissue contacting surface 104. Translation of pusher 108 in turn causes translation of a corresponding pusher plate 108c through a corresponding retention slot 230 toward tissue contacting surface 104 to eject fasteners 110 from the corresponding retention slots 230.

Referring now to FIGS. 14-16, each drive bar 302 and firing cam 304 includes a camming slot 310 having a proximal portion 310a and a distal portion 310b. Distal portion 310b includes an opening 312, a firing cam surface 314 and a retracting cam surface 316. Opening 312 is configured to receive pusher base 108d therethrough such that the proximal cam surface 108e of pusher base 108d engages firing cam surface 314 during distal translation of the firing cam 304. Firing cam surface 314 is sloped such that as proximal cam surface 108e of pusher base 108d slides along firing cam surface 314, pusher 108 is urged toward tissue contacting surface 104 from a pre-fired position to a fired position. As pusher 108 is urged toward tissue contacting surface 104, the corresponding pusher plate 108c translates through the corresponding retention slot 230 to drive the fastener 110 disposed in the retention slot 230 through the opening 230a of tissue contacting surface 104, through tissue disposed between anvil assembly 22 and cartridge assembly 20, and against a staple forming pocket 22a of anvil assembly 22.

Once the pusher base 108*d* reaches the fired position at a top portion 314*a* of firing cam surface 314, drive bar 302 and firing cam 304 are further translated distally such that pusher base 108*d* slides along camming slot 310 towards proximal portion 310*a*. Proximal portion 310*a* of camming slot 310 is dimensioned such that as drive bar 302 and firing cam 304 continue to translate distally, pusher base 108*d* remains in the fired position. This allows the corresponding pusher plate 108*c* to remain in a position which at least partially blocks or covers the opening 232 of retention slot 230 (FIG. 18) to inhibit loading of the next fastener 110 from the corresponding magazine 244 associated with the respective retention slot 230. Camming slot 310 extends a sufficient distance along drive bar 302 to accommodate a full firing stroke of firing cam assembly 300 where, for example, when drive bar 302 and firing cam 304 are in a distal most position, a proximal end 310*c* of camming slot 310 is disposed adjacent to or proximal of the proximal most pusher 108.

During refraction of firing cam assembly 300 after the firing stroke, the distal cam surfaces 108*f* of pushers 108 are engaged by retracting cam surface 316 as drive bar 302 and firing cam 304 are translated proximally and are driven along retracting cam surface 316 toward opening 312 of camming slot 310 to return the pusher 108 from the fired position to the pre-fired position. As each pusher 108 slides along retracting cam surface 316 of firing cam 304 toward the pre-fired condition, the corresponding pusher plate 108*c* translates toward a base of the corresponding retention slot 230 and opens up or uncovers the opening 232 of the corresponding retention slot 230 to the corresponding magazine 244. Once opening 232 is uncovered, retention slot 230 receives the next fastener 110 from the magazine 244 due to the biasing force of biasing member 246. Once firing cam assembly 300 is fully retracted and each retention slot 230 has been loaded with a new fastener 110 from a corresponding magazine 244, surgical stapling apparatus 10 is ready to perform an additional firing stroke.

Referring now to FIGS. 4 and 6-10 the assembly of cartridge assembly 20 will now be described. With reference to FIGS. 4 and 9, a staple pusher 108 is positioned in operative association with each retention slot 230 with pusher base 108*d* being disposed in one of longitudinal slots 205 of each half 226, 228 of each cartridge 206, 208. Fasteners 110 are loaded into retention slots 230 and magazines 244 through the "U" or "H" shaped channels 248 and the biasing members 246 are inserted into the channels 244*a* of the magazines 244 such that legs 246*b*, 246*c* extend into the vertical segments 248*a*, 248*b* of channels 248 and bias the fasteners 110 toward retention slots 230.

Once the components of each half 226, 228 of each cartridge 206, 208 have been assembled, inner and outer halves 226, 228 of each cartridge 206, 208 are joined or coupled together with the flanges 240 and channels 242 of each half 226, 228 interlocking. The assembled inner and outer halves 226, 228 are then inserted into the cartridge support channel 254 which maintains inner and outer halves 226 and 228 in engagement with one another.

Referring now to FIGS. 6 and 7, the assembled cartridges 206, 208 are joined together at the distal end portion 216 by inner tab 224 and inner hole 222 so as to define the central longitudinal slot 252 therebetween and the joined cartridges 206, 208 are inserted into elongated support channel 204 of carrier 202 such that tabs 210 disposed on cartridges 206, 208 are engaged with slots 212 of carrier 202 and support struts 214 of cartridges 206, 208 rest on the side walls of carrier 202. The cartridge assembly 20 is now assembled and ready for use.

The operation of surgical stapling device 10 during a surgical procedure will now be discussed with reference to FIGS. 1, 4A, 12, 13, and 16-18. During the surgical procedure, the surgeon attaches the loading unit 16 to the elongated body 14 and inserts the loading unit 16 into the surgical site. The surgeon then positions tissue between cartridge assembly 20 and anvil assembly 22 and actuates handle assembly 12 to approximate the anvil assembly 22 with the cartridge assembly 20 to grasp the tissue disposed therebetween, as described above. The surgeon further actuates handle assembly 12 to drive firing cam assembly 300 distally through cartridge assembly 20 to fire the surgical fasteners. It is contemplated that a single actuation of handle assembly 12 by the surgeon may grasp tissue and fully fire the surgical stapling device 10. Alternatively, grasping tissue and firing of the surgical stapling device may require multiple actuations of handle assembly 12 with each actuation advancing firing cam assembly 300 a predetermined distance through DLU 16. It is contemplated that the handle portion can be a motorized handle assembly. Such motorized handle assembly can include a controller and/or power source.

As firing cam assembly 300 translates through cartridge assembly 20, each pair of drive bars 302*a*-302*d* and attached pairs of firing cams 304*a*-304*d* translate through respective longitudinal slots 250 of one of inner and outer halves 226, 228, of cartridges 206, 208. During distal translation of firing cams 304*a*-304*d*, each firing cam 304 individually engages each pusher 108 of each cartridge 206, 208 and sequentially drives each pusher 108 towards the tissue engaging surface 104 and thereby eject fasteners 110 from the retention slots 230 disposed in cartridges 206, 208.

As discussed above, with reference to FIGS. 16-19, as each firing cam 304 engages each pusher 108, the proximal cam surface 108*e* of each pusher 108 engages the firing cam surface 314 of each firing cam 304 and is driven up the firing cam surface 314 from the pre-fired position to the fired position, e.g., towards tissue contacting surface 104. As each pusher 108 is driven towards tissue contacting surface 104, each pusher plate 108*c* translates through a corresponding retention slot 230 to eject a corresponding fastener 110 from the corresponding retention slots 230 through a respective opening 230*a* in tissue contacting surface 104, through tissue disposed between anvil assembly 22 and cartridge assembly 20, and against staple forming pockets 22*a* of anvil assembly 22, thereby forming each fastener 110. As the firing cam 304 continues to translate distally, pusher base 108*d* travels along camming slot 310 toward proximal end portion 310*a* and is maintained in the fired position, e.g., driven toward tissue contacting surface 104, such that the corresponding pusher plate 108*c* blocks or covers the opening 232 between the retention slot 230 and the corresponding magazine 244. As firing cam assembly 300 translates distally, knife assembly 308 also translates distally through central longitudinal slot 252 to sever the tissue held between the cartridge assembly 20 and anvil assembly 22.

Once the firing stroke is complete, with firing cam assembly 300 disposed in a distal most position, the surgeon withdraws retraction member 34 proximally to translate firing cam assembly 300 proximally. As firing cam assembly 300 translates proximally through cartridge assembly 20, firing cams 304 are translated proximally through longitudinal slots 250 such that the distal cam surface 108*f* of each pusher base 108*d* engages the retracting cam surface 316 to drive the pusher base 108*d* down toward opening 312 and the pre-fired position. As each pusher base 108*d* is driven toward opening 312, each pusher is translated away from tissue contacting surface 104 and each pusher plate 108*c* is translated away from tissue contacting surface 104 toward the pre-firing position within a corresponding retention slot 230. As each pusher plate 108c is withdrawn to the pre-firing position, the opening 232 between the retention slot 230 and the corresponding magazine 244 is opened or uncovered to allow the next fastener 110 to be received within the retention slot 230 due to the biasing force "F" of the corresponding biasing member 246. Once firing cam assembly 300 is fully translated proximally to a pre-firing position, each retention slot 230 has been reloaded and surgical stapling apparatus 10 is ready for a second firing stroke. In this manner, each retention slot 230 is reloaded in-situ and ready for subsequent use without requiring the surgeon to withdraw the loading unit 16 from the surgical site or replace the loading unit.

It is contemplated that each loading unit 16 may be configured for multiple firing strokes.

In any of the embodiments disclosed herein, the drive bars 302 can be configured as more than one bar partially attached to each other. As shown in FIG. 15, each drive bar is comprised of two drive bars. Each bar can be attached, or partially attached, to at least one other adjacent bar, in any of the embodiments disclosed herein. They may be attached by adhesives or welding. For example, a drive bar comprised of two bars are welded together at the distal end, near the cam surface. Each staple pusher is driven by a pair of such cam bar assemblies, as described in par. 0079 thru 0085. The assembly has better flexibility and permits articulation. Welding two or more bars together gives the bar assembly more stiffness and is desirably welded near the cam surface 304. In any of the embodiments disclosed herein, a pair of relatively thinner bars is used, instead of a single relatively thicker bar, which are at least partially attached to one another.

It is contemplated that individual features of the above described embodiments may be combined without departing from the scope of the present disclosure.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical stapling apparatus comprising:
a body;
an anvil assembly; and
a staple cartridge assembly including:
a first staple cartridge positionable in a channel of the staple cartridge assembly, the first staple cartridge including:
a first staple half including a first row of retention slots;
a second staple half including a second row of retention slots, the second staple half releasably attachable to the first staple half;
a third row of retention slots being alternately disposed in the first staple half and the second staple half of the first staple cartridge, the third row of retention slots disposed between the first and second rows of retention slots;
a plurality of fasteners disposed in the retention slots of the first, second, and third rows; and
a plurality of pushers disposed in the first, second, and third rows of retention slots, the plurality of pushers configured to eject a respective fastener of the plurality of fasteners from its respective retention slot during firing of the surgical stapling apparatus.

2. The surgical stapling apparatus according to claim 1, wherein the staple cartridge assembly further includes a second staple cartridge, the first and second staple cartridges configured to couple together at a distal end portion thereof and define a longitudinal slot therebetween when coupled together, the second staple cartridge including:
a first staple half including a first row of retention slots;
a second staple half including a second row of retention slots, the second staple half releasably attachable to the first staple half;
a third row of retention slots being alternately disposed in the first staple half and the second staple half of the second staple cartridge, the third row of retention slots disposed between the first and second rows of retention slots;
a plurality of fasteners disposed in the retention slots of the first, second, and third rows; and
a plurality of pushers disposed in the first, second, and third rows of retention slots, the plurality of pushers configured to eject a respective fastener of the plurality of fasteners from its respective retention slot during firing of the surgical stapling apparatus.

3. The surgical stapling apparatus according to claim 2, wherein the longitudinal slot is configured to facilitate passage of a knife blade therethrough.

4. The surgical stapling apparatus according to claim 1, wherein the first and second staple halves of the first staple cartridge include corresponding flanges and channels, the channels of the first and second staple halves being configured to receive corresponding flanges of the first and second staple halves, respectively, when the first and second staple halves are coupled together.

5. The surgical stapling apparatus according to claim 4, wherein the flanges of the first and second staple halves include the retention slots of the third row of retention slots therein.

6. The surgical stapling apparatus according to claim 1, wherein the channel of the first staple cartridge is configured to maintain the first and second staple halves in engagement with one another.

7. The surgical stapling apparatus according to claim 1, wherein each retention slot of the first staple cartridge includes a staple magazine disposed in operative association therewith and including a plurality of fasteners therein, the staple magazine being configured to supply one fastener from the plurality of fasteners of the staple magazine to the corresponding retention slot after a firing of the surgical stapling apparatus.

8. The surgical stapling apparatus according to claim 7, wherein the plurality of fasteners disposed in the retention slots and staple magazines of the first row of retention slots have a first size, the plurality of fasteners disposed in the retention slots and staple magazines of the second row of retention slots have a second size, and the plurality of fasteners disposed in the retention slots and staple magazines of the third row of retention slots have a third size.

9. The surgical stapling apparatus according to claim 8, wherein the first size is greater than the third size and the third size is greater than the second size.

10. The surgical stapling apparatus according to claim 1, wherein the first staple half of the first staple cartridge defines a first tissue contacting surface, the second staple half of the first staple cartridge defines a second tissue contacting surface, and the first and second staple halves, when coupled together, define a third tissue contacting surface, and wherein a height of the first tissue contacting surface is smaller than a height of the third tissue contacting surface, and the height of the third tissue contacting surface is smaller than a height of the second tissue contacting surface.

11. The surgical stapling apparatus according to claim 7, wherein the staple magazine includes a biasing member configured to bias the plurality of fasteners disposed in the staple magazine toward the corresponding retention slot.

12. The surgical stapling apparatus according to claim 1, wherein each pusher of the plurality of pushers includes at least one pusher plate disposed within at least one of the first, second, or third rows of retention slots, the at least one pusher plate configured to translate through the respective retention slot to eject the respective fastener disposed therein.

13. The surgical stapling apparatus according to claim 7, wherein each pusher of the plurality of pushers is configured to cover an opening disposed between a respective retention slot and the corresponding staple magazine when translating through the respective retention slot to a fired position to eject the respective fastener disposed therein, and to uncover the opening disposed between the respective retention slot and the corresponding staple magazine when translating back to a pre-fired position after the respective fastener has been ejected from the respective retention slot, thereby allowing the corresponding staple magazine to re-supply the respective retention slot with one fastener from the plurality of fasteners disposed in the corresponding staple magazine.

14. The surgical stapling apparatus according to claim 1, further including a disposable loading unit releasably coupled at a distal end of the body and configured to support the anvil assembly and the staple cartridge assembly thereon, the disposable loading unit including a firing cam assembly translatably disposed therein and including a plurality of drive bars, each drive bar of the plurality of drive bars including a firing cam disposed at a distal end thereof and configured to translate through one of the first and second staple halves of the first staple cartridge to individually engage and drive each pusher of the plurality of pushers disposed in the first, second, and third rows of retention slots to eject a fastener from the plurality of fastener from the corresponding retention slot during firing of the surgical stapling apparatus.

15. The surgical stapling apparatus according to claim 14, wherein each of the first and second staple halves of the first staple cartridge includes a longitudinal slot extending therethrough, the longitudinal slot being configured for the reception of a drive bar of the plurality of drive bars therethrough.

16. The surgical stapling apparatus according to claim 14, wherein each pusher of the plurality of pushers includes a proximal camming surface and each firing cam includes a firing cam surface, the firing cam surface being configured to engage the proximal camming surface of the pusher during distal translation of the respective drive bar to translate the pusher to the fired position and cause the pusher to eject the respective fastener from the corresponding retention slot.

17. The surgical stapling apparatus according to claim 14, wherein each pusher of the plurality of pushers includes a distal camming surface and each firing cam includes a retracting cam surface, the retracting cam surface being configured to engage the distal camming surface of the pusher during proximal translation of the respective drive bar to cause the pusher to return to the pre-fired position.

18. The surgical stapling apparatus according to claim 1, further comprising:
a handle assembly, the body extending distally from the handle assembly;
the staple cartridge assembly further including a staple magazine disposed in operative association with each retention slot of the first staple cartridge, the staple magazine including some fasteners of the plurality of fasteners and a biasing member disposed therein, the biasing member configured to bias the fasteners of the staple magazine towards the corresponding retention slot, the staple magazine being configured to reload the corresponding retention slot with a fastener from the fasteners disposed therein after a firing of the surgical stapling apparatus.

19. A staple cartridge assembly for use with a surgical stapling apparatus, the staple cartridge assembly comprising:
a first staple cartridge and a second staple cartridge coupled to the first staple cartridge, each of the first and second staple cartridges including a first staple half and a second staple half, each of the first and second staple halves including a longitudinal slot extending therethrough and a plurality of retention slots disposed thereon, each retention slot including a fastener disposed therein, each of the first and second staple halves of the first and second staple cartridges further including a plurality of pushers disposed therein in operative communication with the respective longitudinal slot and the plurality of retention slots;
a plurality of drive bars, each drive bar of the plurality of drive bars configured to translate through the respective longitudinal slot of one of the first or second staple halves of the first or second staple cartridge, whereby each drive bar of the plurality of drive bars individually engages each pusher of the respective first or second staple half to thereby drive each pusher to sequentially eject the fastener from the associated retention slot upon translation of the drive bar through the longitudinal slot of one of the first or second staple halves.

20. A surgical stapler having an anvil assembly, a cartridge assembly, and a firing cam assembly, the cartridge assembly including two staple cartridges received in a carrier to define a knife slot therebetween, each of the two staple cartridges further includes a first staple half and a second staple half releasably attachable to the first staple half, the cartridge assembly having a plurality of surgical staples disposed in retention slots configured for sequential ejection therefrom and a plurality of staple magazines, each staple magazine disposed adjacent a retention slot and including more than one staple associated therewith.

* * * * *